(12) United States Patent
Harding et al.

(10) Patent No.: US 10,445,855 B2
(45) Date of Patent: Oct. 15, 2019

(54) LUNG SEGMENTATION AND BONE SUPPRESSION TECHNIQUES FOR RADIOGRAPHIC IMAGES

(71) Applicants: ICAD, Inc., Nashua, NH (US); Konica Minolta, Inc., Tokyo (JP)

(72) Inventors: David S. Harding, Austin, TX (US); Sridharan Kamalakanan, Dallas, TX (US); Satoshi Kasai, Hachioji (JP); Shinsuke Katsuhara, Koganei (JP); James H. Pike, Carrollton, TX (US); Muhammad F. Sabir, Allen, TX (US); Jeffrey C. Wehnes, Richardson, TX (US)

(73) Assignees: iCAD, Inc., Nashua, NH (US); Konica Minolta, Inc., Tokyo (JP)

( * ) Notice: Subject to any disclaimer, the term of this patent is extended or adjusted under 35 U.S.C. 154(b) by 0 days.

(21) Appl. No.: 15/302,846

(22) PCT Filed: Apr. 1, 2015

(86) PCT No.: PCT/US2015/023924
§ 371 (c)(1),
(2) Date: Oct. 7, 2016

(87) PCT Pub. No.: WO2015/157067
PCT Pub. Date: Oct. 15, 2015

(65) Prior Publication Data
US 2017/0032535 A1    Feb. 2, 2017

Related U.S. Application Data

(60) Provisional application No. 61/976,971, filed on Apr. 8, 2014.

(51) Int. Cl.
*G06K 9/00*     (2006.01)
*G06T 3/00*     (2006.01)
(Continued)

(52) U.S. Cl.
CPC .......... *G06T 3/0093* (2013.01); *A61B 6/5211* (2013.01); *G06K 9/3233* (2013.01);
(Continued)

(58) Field of Classification Search
None
See application file for complete search history.

(56) References Cited

U.S. PATENT DOCUMENTS 6,011,862 A    1/2000  Doi et al.
8,675,933 B2   3/2014  Wehnes et al.
(Continued)

FOREIGN PATENT DOCUMENTS

JP    H02-273876 A    11/1990
JP    H08-335271 A    12/1996
(Continued)

OTHER PUBLICATIONS

Partial Supplementary European Search Report in counterpart European Application No. 15 77 6656.9 dated Nov. 30, 2017 (10 pages).
(Continued)

*Primary Examiner* — Stephen P Coleman
(74) *Attorney, Agent, or Firm* — Osha Liang LLP

(57) ABSTRACT

Lung segmentation and bone suppression techniques are helpful pre-processing steps prior to radiographic analyzes of the human thorax, as may occur during cancer screenings and other medical examinations. Autonomous lung segmentation may remove spurious boundary pixels from a radiographic image, as well as identify and refine lung boundaries. Thereafter, autonomous bone suppression may identify clavicle, posterior rib, and anterior rib bones using various image processing techniques, including warping and edge detection. The identified clavicle, posterior rib, and anterior (Continued)

rib bones may then be suppressed from the radiographic image to yield a segmented, bone suppressed radiographic image.

11 Claims, 23 Drawing Sheets

(51) Int. Cl.

| | | |
|---|---|---|
| A61B 6/00 | (2006.01) | |
| G06T 7/00 | (2017.01) | |
| G06T 7/73 | (2017.01) | |
| G06T 7/12 | (2017.01) | |
| G06K 9/32 | (2006.01) | |
| G06K 9/34 | (2006.01) | |
| G06K 9/46 | (2006.01) | |
| G06T 5/00 | (2006.01) | |

(52) U.S. Cl.
CPC ........... *G06K 9/342* (2013.01); *G06K 9/4647* (2013.01); *G06T 7/0012* (2013.01); *G06T 7/12* (2017.01); *G06T 7/75* (2017.01); *G06K 2209/051* (2013.01); *G06T 5/002* (2013.01); *G06T 2207/10116* (2013.01); *G06T 2207/20036* (2013.01); *G06T 2207/20076* (2013.01); *G06T 2207/20116* (2013.01); *G06T 2207/30008* (2013.01); *G06T 2207/30061* (2013.01); *G06T 2207/30064* (2013.01)

(56) References Cited

U.S. PATENT DOCUMENTS

| | | | |
|---|---|---|---|
| 8,675,934 | B2 | 3/2014 | Wehnes et al. |
| 8,855,388 | B2 | 10/2014 | Wehnes et al. |
| 8,923,594 | B2 | 12/2014 | Wehnes et al. |
| 9,076,197 | B2 | 7/2015 | Wehnes |
| 9,256,799 | B2 | 2/2016 | Wehnes et al. |
| 2004/0109595 | A1 | 6/2004 | Luo et al. |
| 2005/0100208 | A1 | 5/2005 | Suzuki et al. |
| 2005/0152589 | A1 | 7/2005 | Wehnes et al. |
| 2009/0214099 | A1 | 8/2009 | Merlet |
| 2012/0163682 | A1 | 6/2012 | Sohn et al. |
| 2013/0108135 | A1 | 5/2013 | Huo et al. |

FOREIGN PATENT DOCUMENTS

| | | |
|---|---|---|
| WO | 95/15536 A1 | 6/1995 |
| WO | 99/42031 A1 | 8/1999 |
| WO | 2009/029676 A1 | 3/2009 |
| WO | 2009029676 A1 | 3/2009 |

OTHER PUBLICATIONS

International Search Report issued in corresponding application No. PCT/US2015/023924 dated Jul. 8, 2015 (2 pages).

Written Opinion of the International Searching Authority issued in corresponding application No. PCT/US2015/023924 dated Jul. 8, 2015 (7 pages).

Notification Concerning Transmittal of International Preliminary Report on Patentability and International Preliminary Report on Patentability issued in corresponding International Application No. PCT/US2015/023924, dated Oct. 20, 2016 (9 pages).

Office Action in counterpart Chinese Patent Application No. 201580018405.0 dated Aug. 2, 2018 (15 pages).

Extended European Search Report in counterpart European Application No. 15776656.9 dated May 24, 2018 (10 pages).

Office Action in counterpart Japanese Patent Application No. 2017-505051 dated Oct. 16, 2018 (11 pages).

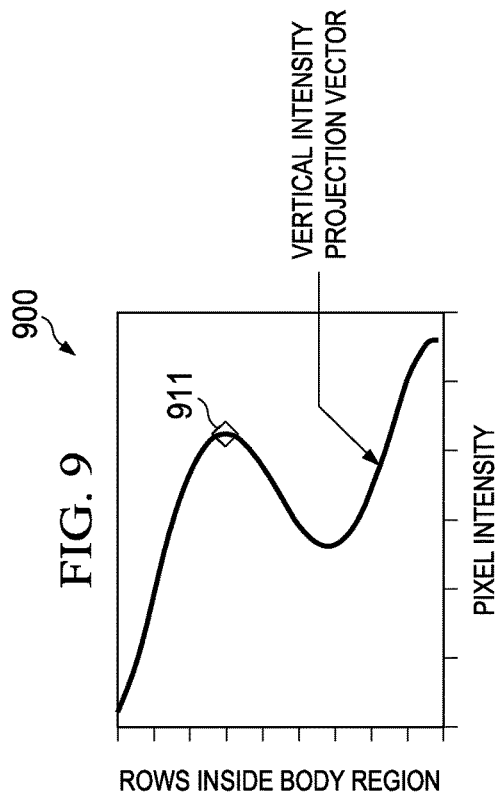
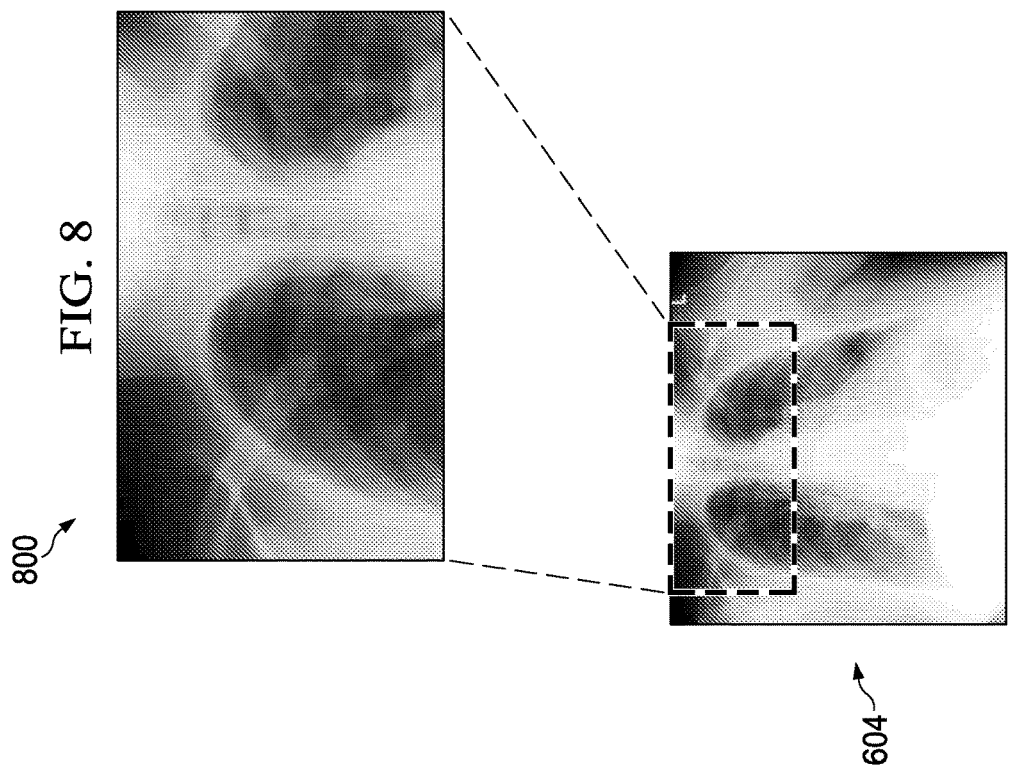

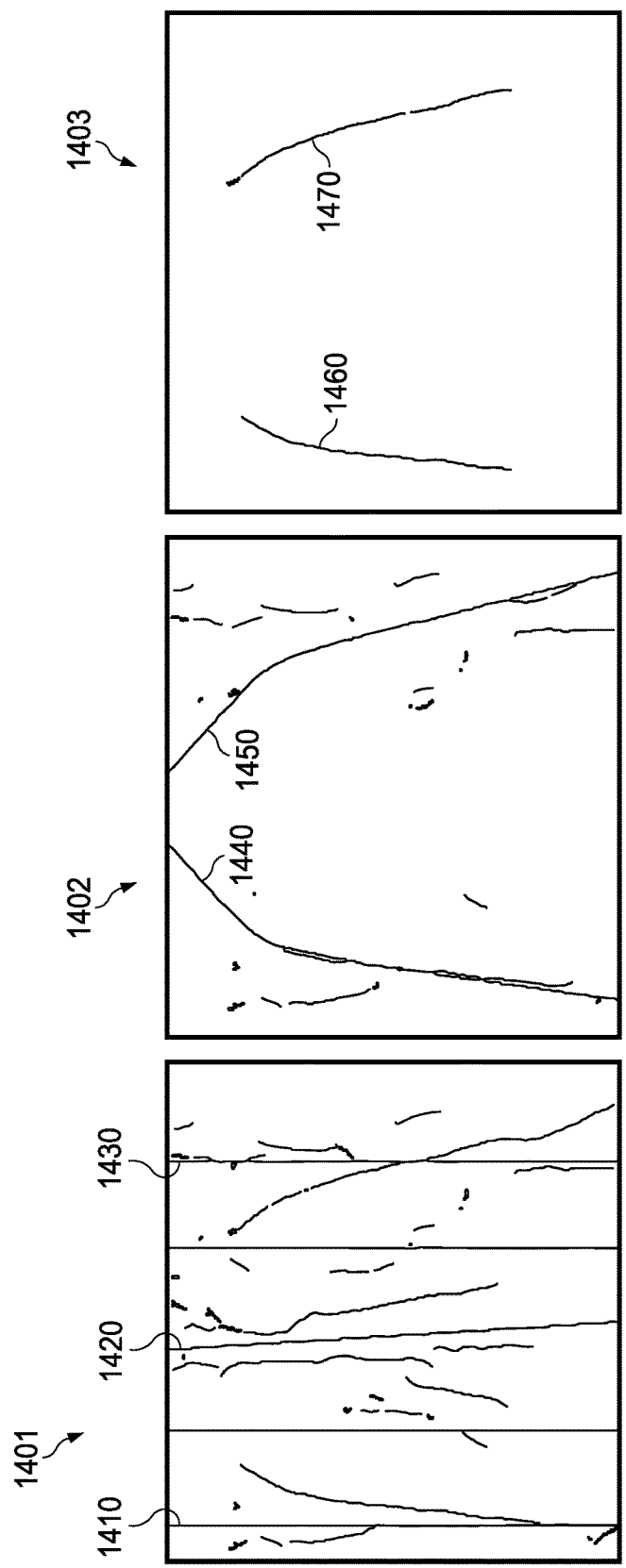

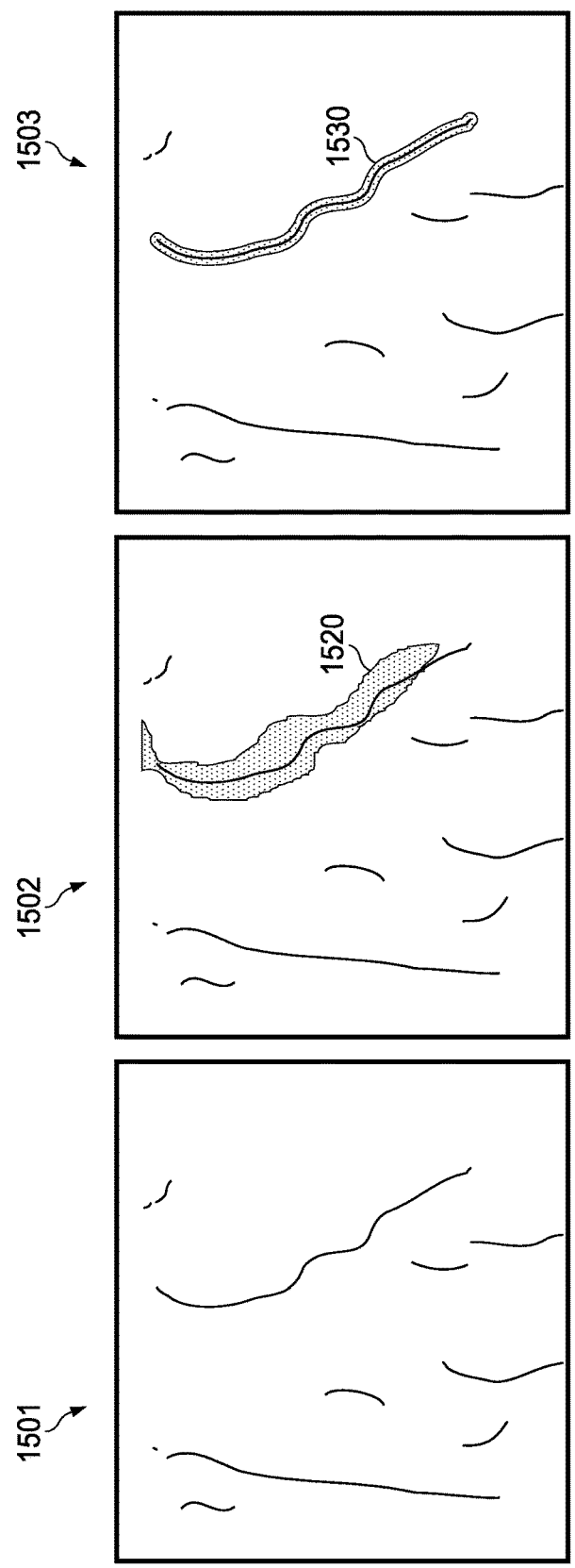

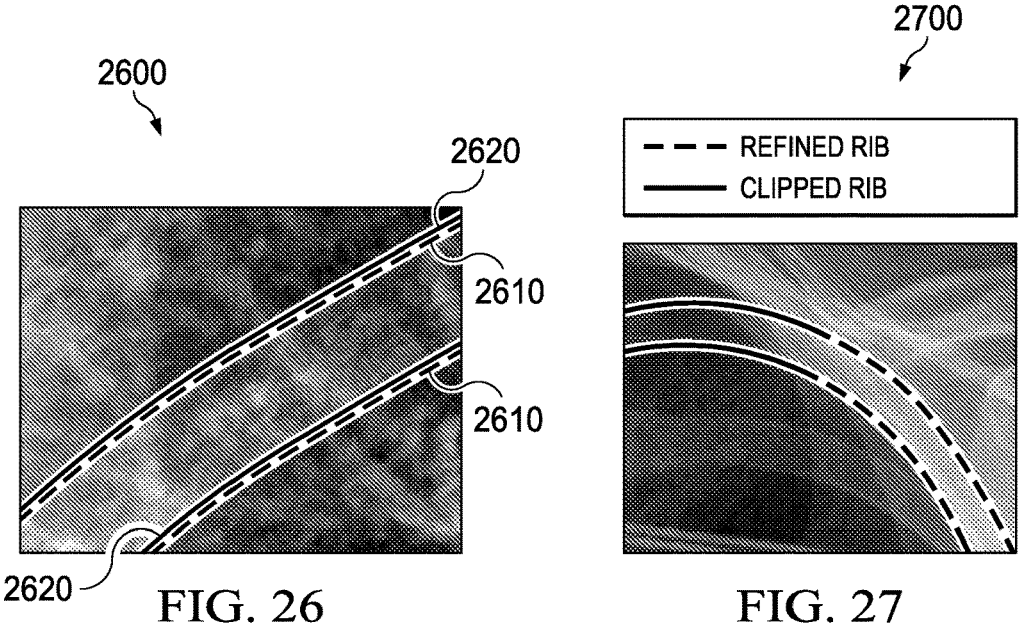
FIG. 26
FIG. 27
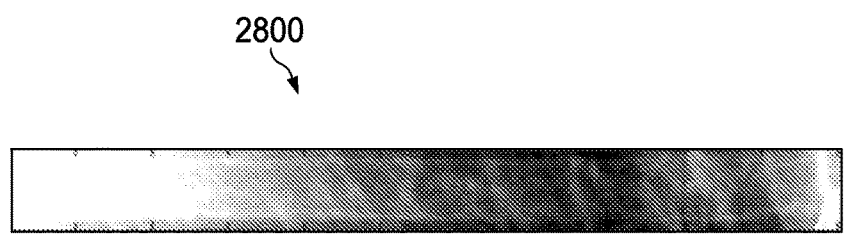
FIG. 28
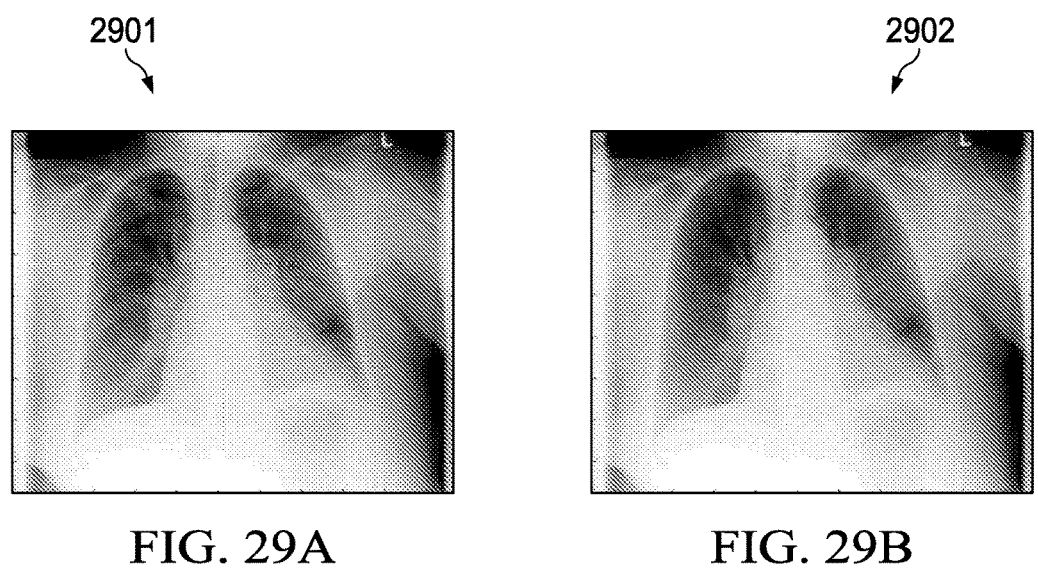
FIG. 29A
FIG. 29B

LUNG SEGMENTATION AND BONE SUPPRESSION TECHNIQUES FOR RADIOGRAPHIC IMAGES

This patent application claims priority to U.S. Provisional Application No. 61/976,971, filed on Apr. 8, 2014 and entitled "Lung Segmentation and Bone Suppression Techniques for Radiographic Images," which is hereby incorporated by reference herein as if reproduced in its entirety.

TECHNICAL FIELD

The present invention relates to medical imaging, and, in particular embodiments, to lung segmentation and bone suppression techniques for radiographic images.

BACKGROUND

Lung segmentation is a used for various tasks related to the analysis of the lungs in radiographic images, e.g. X-Rays, etc. For example, lung segmentation is often used to diagnose emphysema, and is also a preprocessing step for the segmentation of other lung structures and anomalies, such as vessels, fissures, lobules, and nodules. Bone suppression is also commonly performed on radiographic images prior to diagnosis. Accordingly, techniques for accurately performing lung segmentation and bone suppression in radiographic images are desired.

SUMMARY OF THE INVENTION

Technical advantages are generally achieved, by embodiments of this disclosure which describe lung segmentation and bone suppression techniques for radiographic images.

In accordance with an embodiment, a method for performing lung segmentation is provided. In this example, the method includes receiving a radiographic image, identifying region of interest (ROI) boundaries within the radiographic image, identifying lung boundaries in accordance with the ROI boundaries, and merging the lung boundaries to generate a segmented lung structure.

In accordance with another embodiment, a method for performing bone suppression is provided. In this example, the method includes receiving a radiographic image, and detecting bones in the radiographic image. The detected bones include one or a combination of a clavicle bone, a posterior rib bone, and an anterior rib bone. The method further includes suppressing the detected bones in the radiographic image to generate a bone suppressed image.

In accordance with yet another embodiment, a method for performing bone suppression is provided. In this example, the method includes receiving a radiographic image, performing lung segmentation on the radiographic image to generate a segmented lung image, detecting clavicle bones in the segmented lung image, detecting rib bones in the segmented lung image, and suppressing the detected bones from the radiographic image to generate a bone suppressed image.

BRIEF DESCRIPTION OF THE DRAWINGS

For a more complete understanding of the present disclosure, and the advantages thereof, reference is now made to the following descriptions taken in conjunction with the accompanying drawings, in which:

FIG. 8 illustrates a diagram of yet another embodiment radiographic image;

FIG. 9 illustrates a graph of a smoothed vertical intensity projection vector;

FIGS. 14A-14C illustrate diagrams of zero-crossing points associated with radiographic images;

FIGS. 15A-15C illustrate diagrams of additional zero-crossing points associated with radiographic images;

FIG. 26 illustrates a diagram of yet another embodiment radiographic image;

FIG. 27 illustrates a diagram of yet another embodiment radiographic image;

FIG. 28 illustrates a diagram of yet another embodiment radiographic image;

FIGS. 29A-29B illustrate diagrams of yet additional embodiment radiographic images.

DETAILED DESCRIPTION OF ILLUSTRATIVE EMBODIMENTS

The making and using of embodiments of this disclosure are discussed in detail below. It should be appreciated, however, that the concepts disclosed herein can be embodied in a wide variety of specific contexts, and that the specific embodiments discussed herein are merely illustrative and do not serve to limit the scope of the claims. Further, it should be understood that various changes, substitutions and alterations can be made herein without departing from the spirit and scope of this disclosure as defined by the appended claims.

Aspects of this disclosure provide embodiment lung segmentation techniques for use in analysing X-Rays of the human thorax. Embodiment lung segmentation techniques remove spurious boundary pixels from an input image to obtain a protected area, and compute a rough lung region of interest (ROI) from the protected area using anatomy and/or image based information. Thereafter, lung contours/boundaries within the region of interest are identified, refined, and merged to generate a lung segmentation result, e.g., a segmented lung structure. These and other aspects are discussed in greater detail below.

Figure 1:
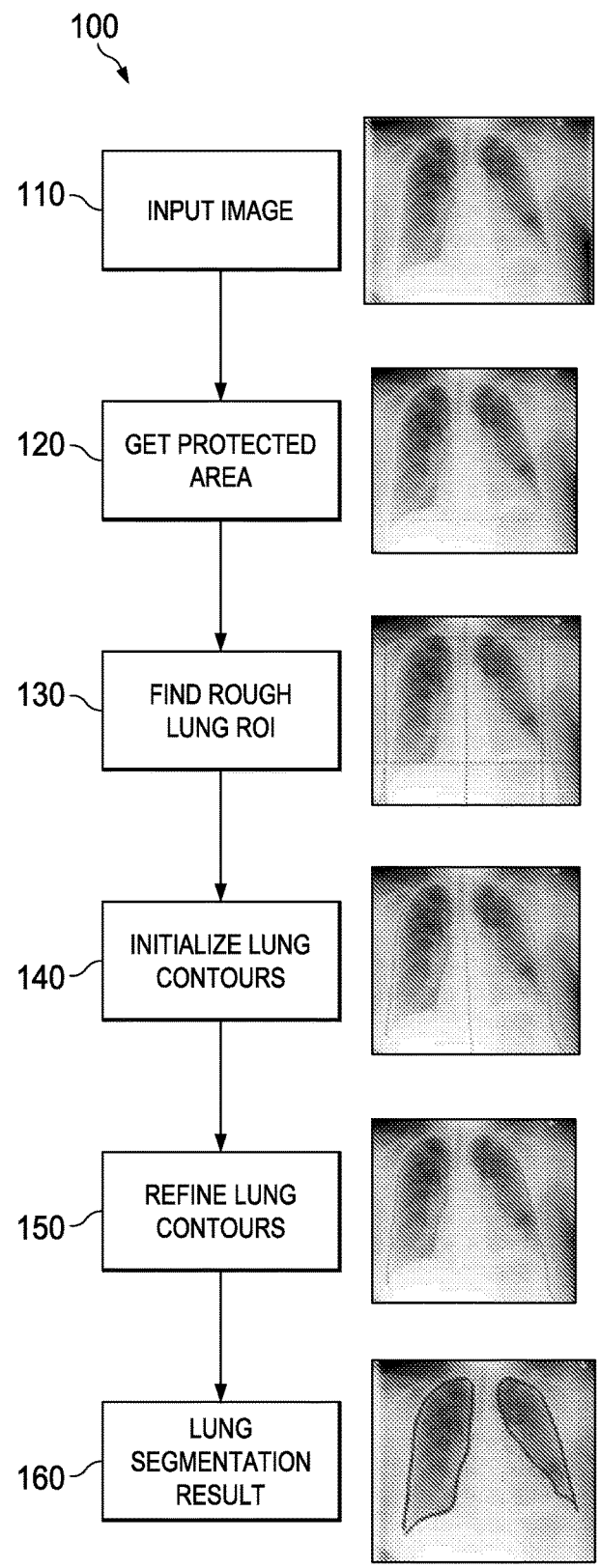
FIG. 1 illustrates a flowchart of an embodiment method for performing lung segmentation.

FIG. 1 illustrates an embodiment method 100 for performing lung segmentation. As shown, the method 100 begins at step 110, where an input image is obtained. The input image may be a radiographic image of a human thorax. Next, the method 100 proceeds to step 120, where spurious boundary pixels are removed to obtain a protected area, which may be an area comprised primarily of relevant attributes. Spurious boundary pixels may correspond to, inter alia, deceptive pixel values located at the boundary between tissues having different densities (e.g., the boundary between bone and soft-tissue), and may lead to false classifications of lung structures (e.g., nodules, etc.) during and/or following lung segmentation. Thereafter, the method 100 proceeds to step 130, where a region of interest is identified within the protected area. The region of interest may correspond to a rough area or grid (e.g., formed by vertical and horizontal lines) encompassing the primary lung structures. Next, the method 100 proceeds to step 140, where lung contours are initialized. Lung contours may correspond to curved lung boundary lines that outline the lungs. Thereafter, the method 100 proceeds to steps 150 and 160, where the lung contours are refined and merged to produce a lung segmentation result. Techniques for performing each of these steps are explained in greater detail below.

Embodiment techniques obtain a protected area by at least partially eliminating spurious pixels from a radiographic image. Spurious pixels include any pixel value that is non-representative of the object (e.g., human thorax) depicted in the radiographic image. Spurious pixels may include spurious boundary pixels, which are non-representative pixel values positioned at the boundary between different density regions in a radiographic image.

Figure 2A:
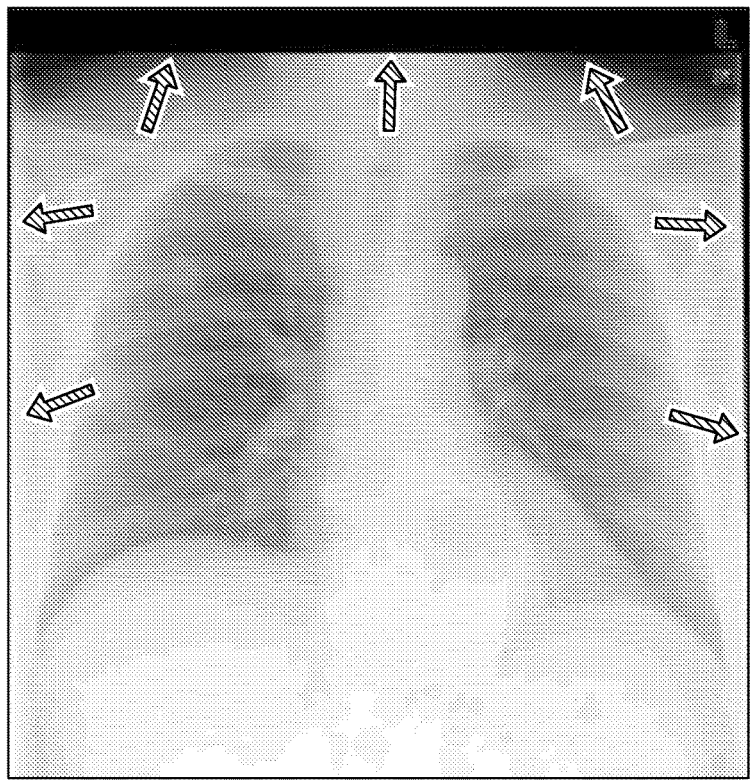
FIGS. 2A-2B illustrate diagrams of embodiment radiographic images.
Figure 2B:
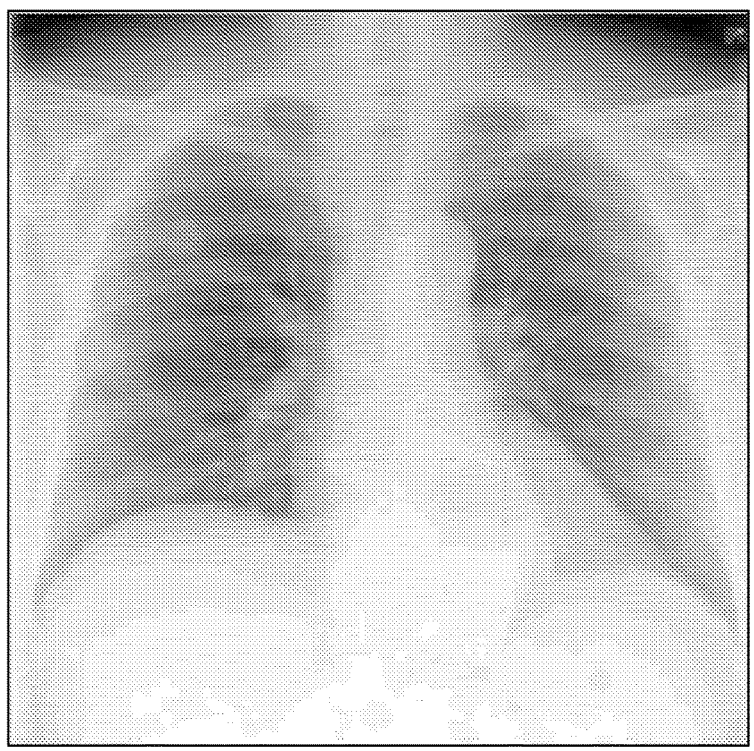

Spurious boundary pixels may include dark boundary bands located along the image boundary. FIG. 2A illustrates a radiographic image 201 that includes dark boundary bands, as indicated by the arrows. Aspects of this disclosure provide techniques for cropping the radiographic image to remove the dark boundary bands. FIG. 2B illustrates a cropped output image 202 of the radiographic image 201 in which many of the dark boundary bands have been removed. Dark boundary bands can be identified by performing a search from the borders of the radiographic image, e.g., from the top, bottom, left and right edges of the image. In some embodiments, the search is performed on an area up to one-third of the radiographic image in that particular direction. A band may be considered dark if the ratio of low intensity pixels along that particular band exceeds a threshold. In one example, a band is considered dark if at least sixty percent of pixels along that band have a low intensity value. The image is cropped to remove detected bands positioned at least a threshold distance away from the image boundary to obtain a cropped output image. In one embodiment, the image is cropped to remove dark bands positioned farthest away from the image boundaries.

Figure 3A:
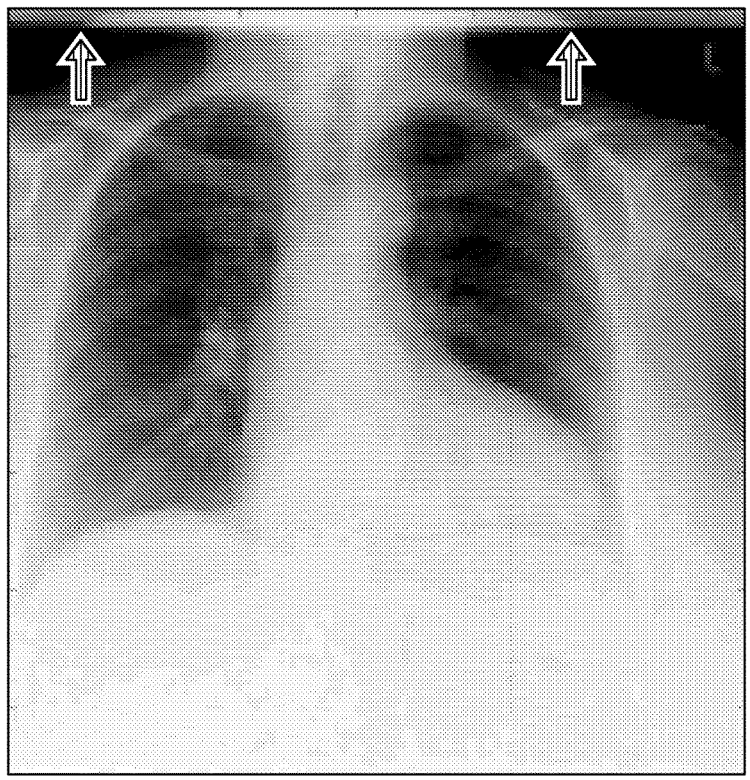
FIGS. 3A-3B illustrate diagrams of additional embodiment radiographic images.
Figure 3B:
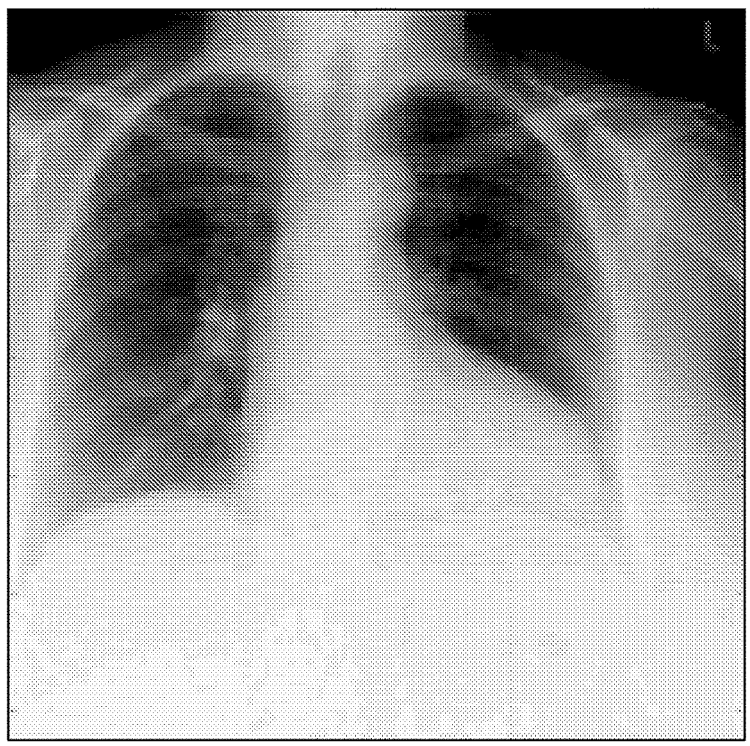

Spurious boundary pixels may also include high variance boundaries. FIG. 3A illustrates a radiographic image 301 that includes high variance boundaries, as indicated by the arrows. Aspects of this disclosure provide techniques for cropping the radiographic image to remove high variance boundaries. FIG. 3B illustrates a cropped output image 302 of the radiographic image 301 in which many of the high variance boundaries have been removed. To crop high variance boundaries, the radiographic image is divided into overlapping blocks and a variance for each of the overlapping blocks is computed. Candidate blocks with high variance along the image boundaries are identified based on a threshold. Subsequently, the radiographic image is cropped along each boundary based on the selected high variance blocks to obtain the cropped output image.

Figure 4A:
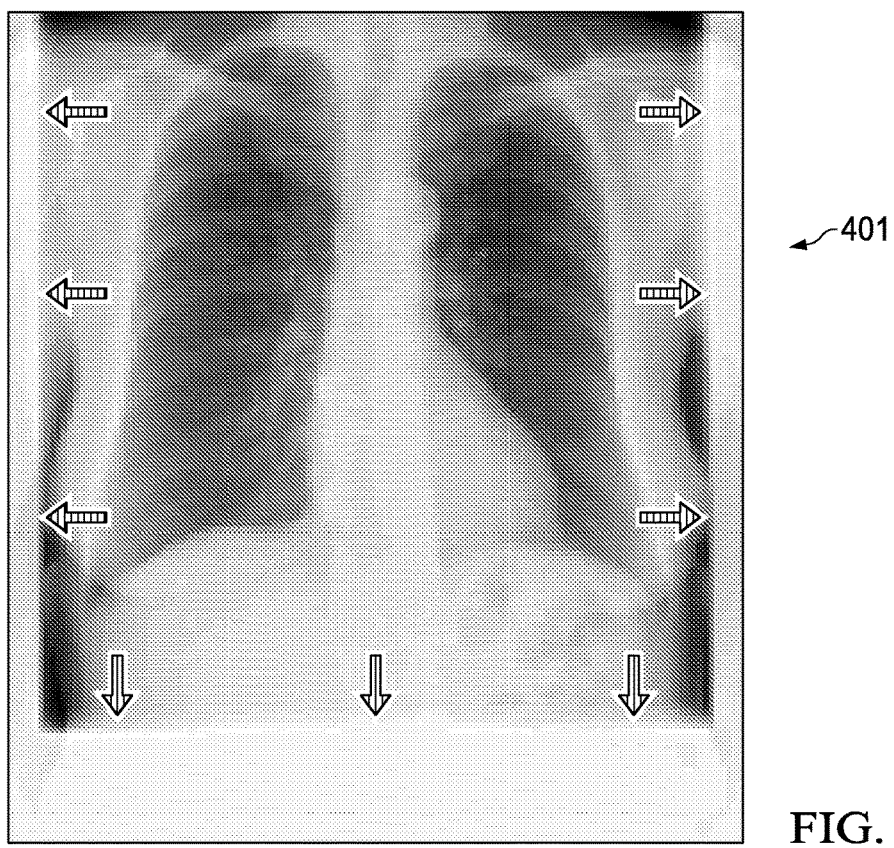
FIGS. 4A-4B illustrate diagrams of yet additional embodiment radiographic images.
Figure 4B:
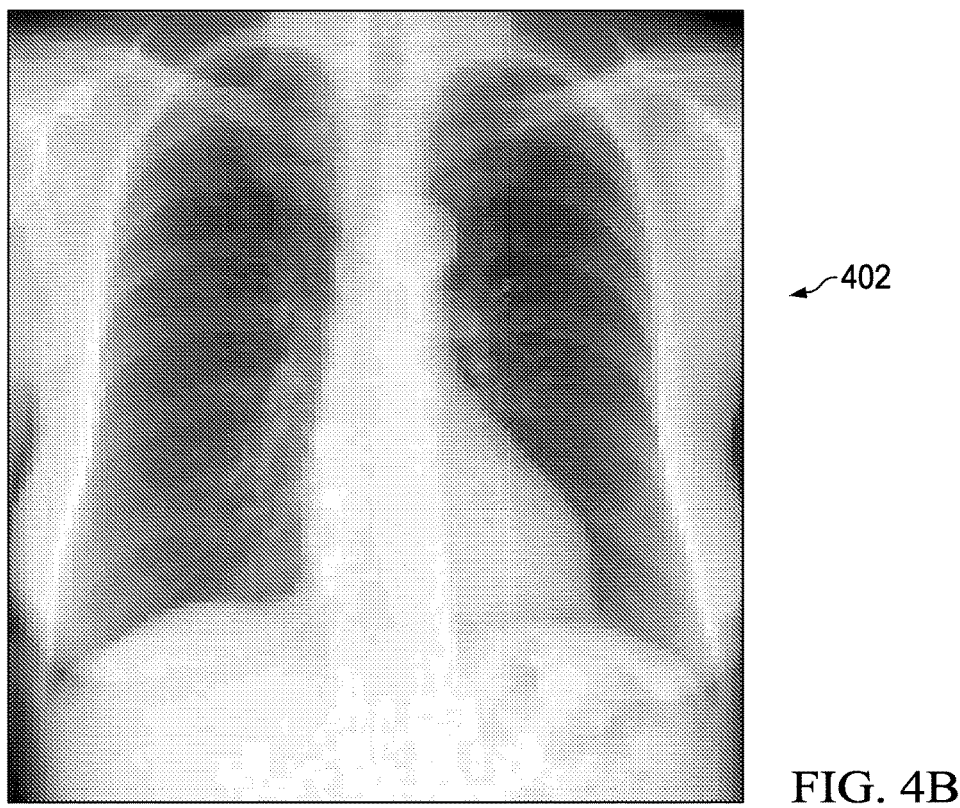

Spurious boundary pixels may also include linear structures. FIG. 4A illustrates a radiographic image 401 that includes linear structures, as indicated by the arrows. Aspects of this disclosure provide techniques for cropping the radiographic image to remove linear structures. FIG. 4B illustrates a cropped output image 402 of the radiographic image 401 in which many of the linear structures have been removed. To remove linear structures, the radiographic image is smoothed using (for example) an isotropic Gaussian filter. Other techniques may also be used to smooth the radiographic image. Next, a first derivative is computed across each boundary direction of the smoothed image, and linear structures are identified based on the computed derivatives. In one example, linear structures within five degrees of the image boundaries are detected based on the computed first derivatives. After the linear structures are identified, the radiographic image is cropped to remove the linear structures and obtain the cropped output image.

Figure 5:
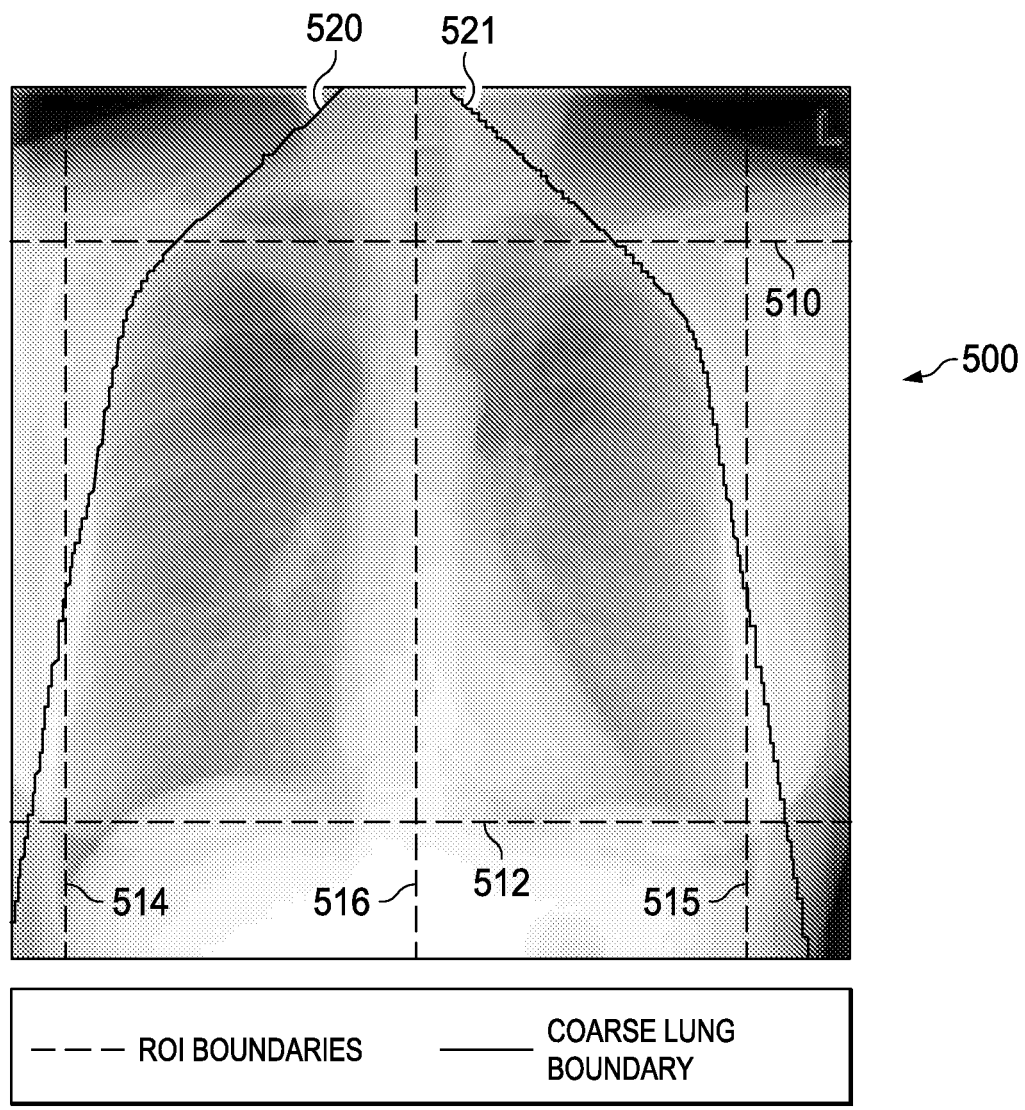
FIG. 5 illustrates a diagram of yet another additional embodiment radiographic image.

After processing the radiographic image to remove spurious pixels, a rough region of interest (ROI) is generated based on the processed image. The region of interest may comprise five control points corresponding to the top, bottom, left, right and middle of the lung region. The control points may be referred to as ROI boundaries throughout this disclosure. For example, the top control point may be referred to as an upper ROI boundary, the bottom control point may be referred to as a lower ROI boundary, the left control point may be referred to as a left ROI boundary, the bottom right point may be referred to as a right ROI boundary, and the central control point may be referred to as a central ROI boundary. FIG. 5 illustrates a radiographic image 500 in which the ROI boundaries 510-516 (dashed lines) and the coarse lung boundaries 520, 521 (solid lines) have been identified. The ROI boundaries 510-516 include an upper ROI boundary 510, a lower ROI boundary 512, a right ROI boundary 514, a left ROI boundary 515, and a center ROI boundary 516.

Embodiment techniques for identifying ROI boundaries may begin by identifying and isolating a body region that represents a patient's torso. The body region may be isolated by identifying pixels representing the body region, and zeroing out pixels positioned outside the body region. The following steps may be used to identify pixels representing the body region: (i) identifying low intensity pixels in the radiographic image (e.g., pixels having pixel intensity values below a threshold); (ii) computing a mean pixel value and a median pixel value for the identified low intensity pixels; (iii) identifying a first group of pixels having an intensity value that is less than the computed mean pixel value; (iii) identifying a second group of pixels having a value that is greater than the computed median pixel value; (iv) performing a connected component analysis on the first and second group of pixels to obtain a largest blob; and (v) obtaining the body region by filling holes in the largest blob using a connected component procedure. Notably, performing the connected component analysis may preserve the largest blob and eliminate the small spurious regions. The largest blob may correspond to the body region, and holes filled in the largest blob may correspond to lower density regions of the lung.

Figure 6A:
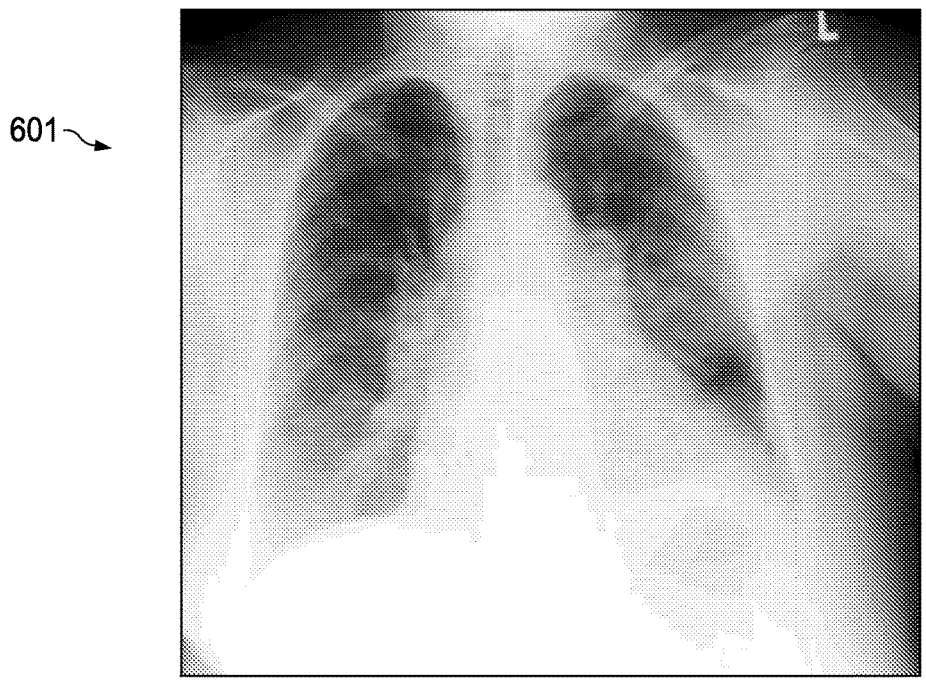
FIGS. 6A-6D illustrate diagrams of yet additional embodiment radiographic images.
Figure 6B:
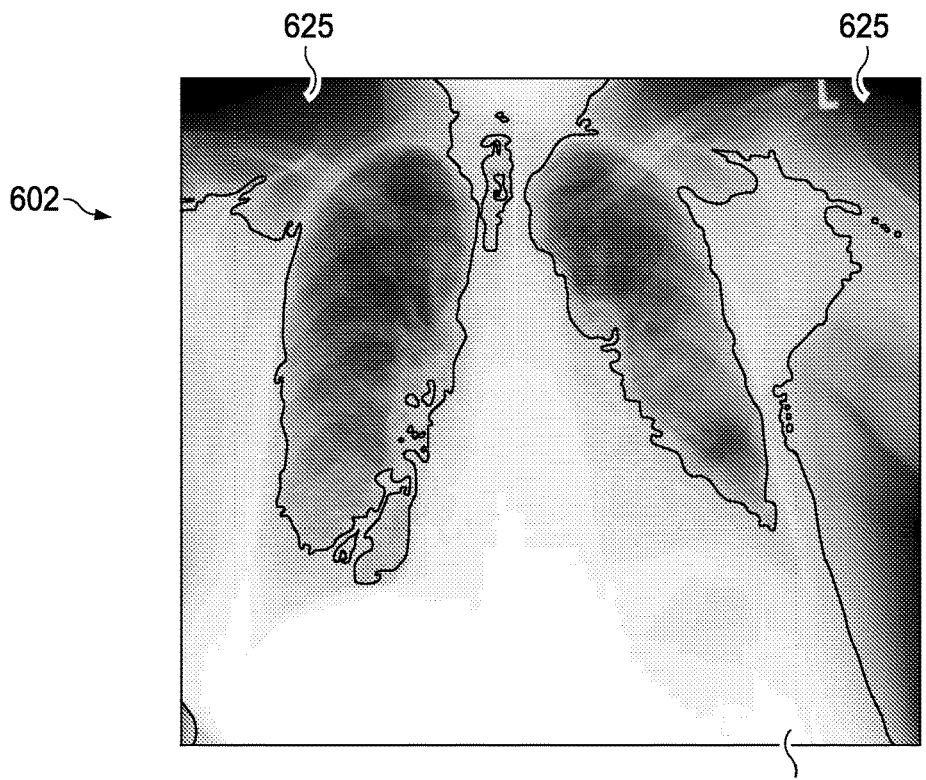

FIG. 6A illustrates a radiographic image 601, while FIG. 6B illustrates a radiographic image 602 identifying regions of pixels 625 having intensity values that are less than a mean value of low intensity pixels in the radiographic image 601.

Figure 6C:
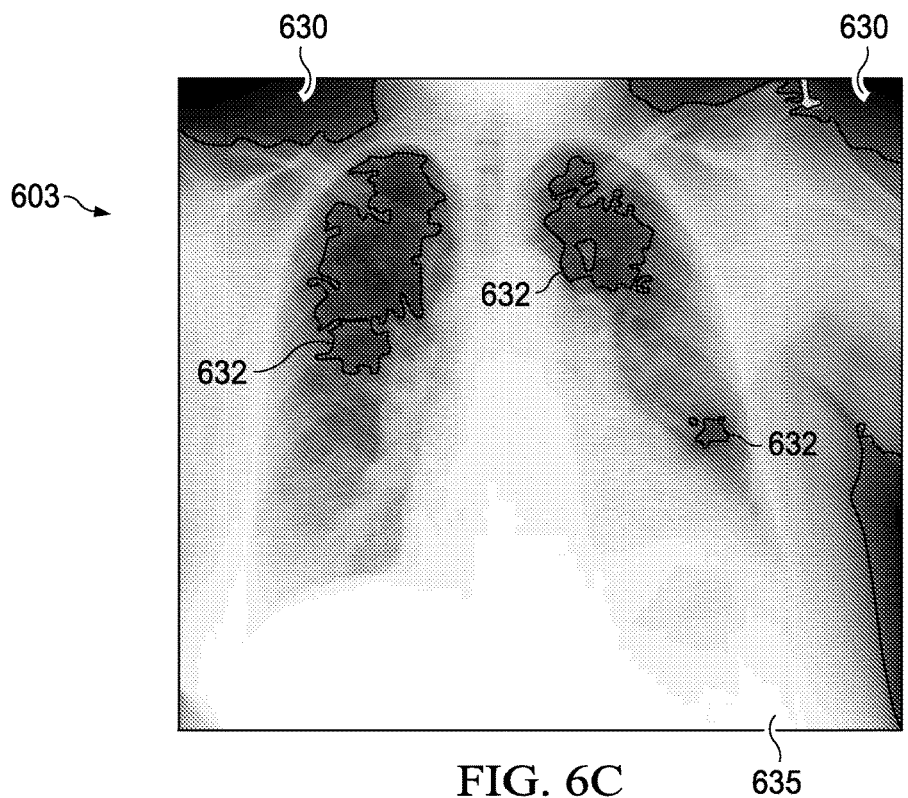
Figure 6D:
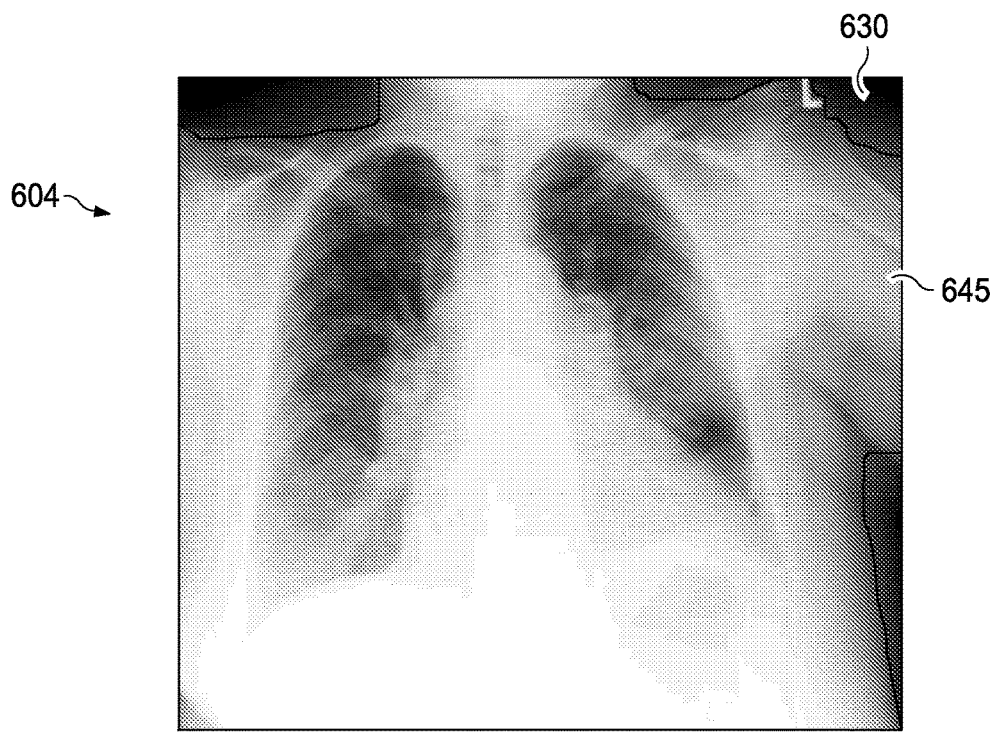

FIG. 6C illustrates a radiographic image 603 identifying spurious pixel regions 630, low intensity lung regions 632, and a largest blob region 635. FIG. 6D illustrates a radiographic image 604 identifying spurious pixel regions 630 and a body region 645. The body region 645 may have been generated by filling holes in the largest blob region 635, where the holes correspond to the low intensity lung regions 632.

Figure 7:
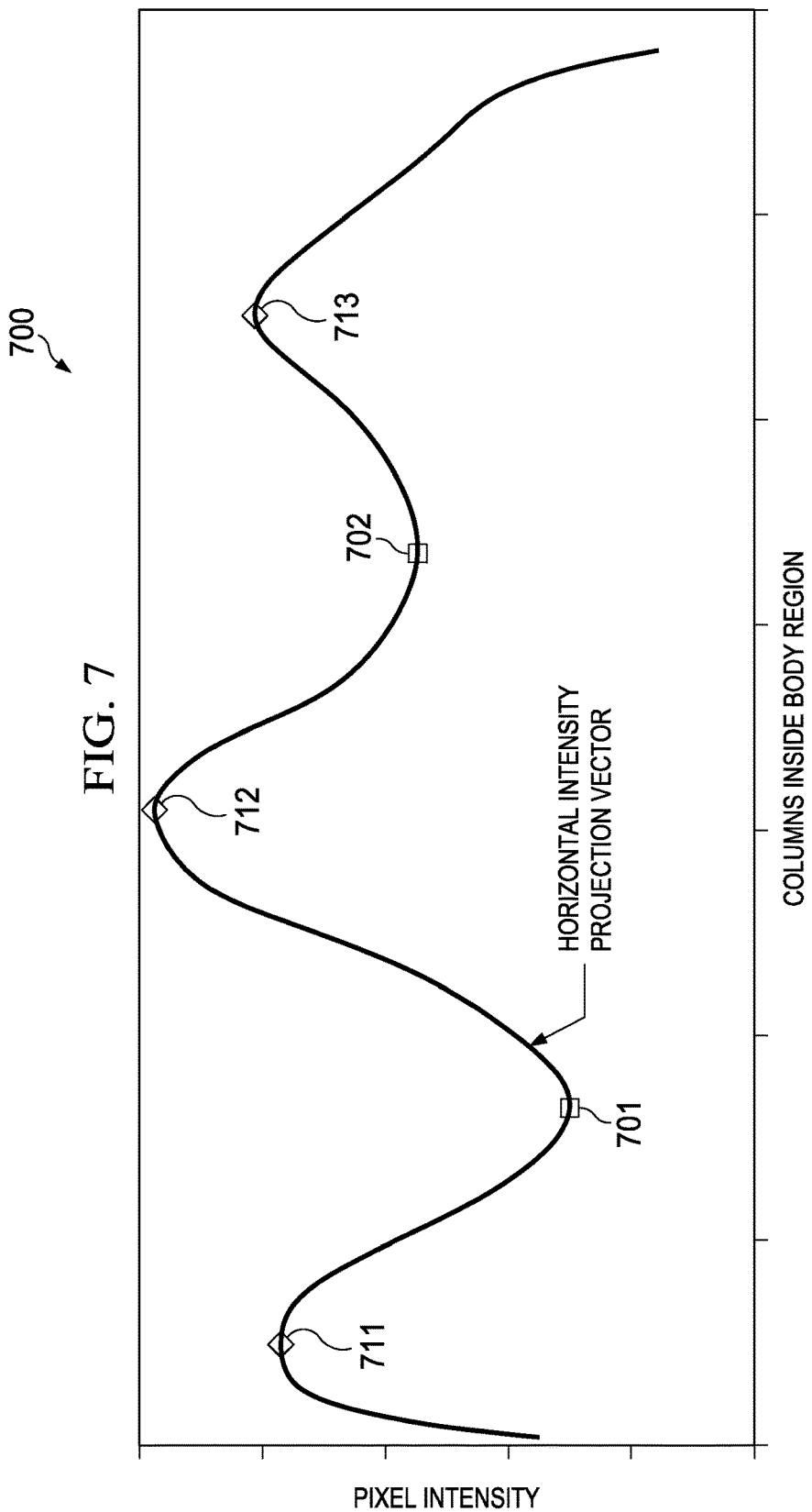
FIG. 7 illustrates a graph of a smoothed horizontal intensity projection vector.

The next step in identifying ROI boundaries may be to identify the mid, left, and right control points. In order to find the mid, left and right control points, a horizontal intensity projection may be computed by summing up the intensity values of each image column inside the body region. The horizontal intensity projection is then smoothed (e.g., using an isotropic Gaussian filter), and then the local maxima and minima of the horizontal intensity projection are computed. FIG. 7 illustrates a graph 700 of a smoothed horizontal intensity projection vector corresponding to the body region 645 of the radiographic image 604. The graph 700 shows local maximums 711-713 and local minimums 701, 702 on the smoothed horizontal intensity projection vector. A mid control point may be selected according to the local maximums 711-713. For example, the mid control point may be selected as the lowest local maxima value that is greater than one third of the length of the horizontal intensity projection vector. As another example, the mid control point may be selected as the highest local maxima value that is less than two-thirds of the length of the horizontal intensity projection vector. The outer left and right control points may be selected based on the right and left maximum values of the projection vector. In some embodiments, the local minimums 701, 702 correspond to the lung center.

The next step in identifying ROI boundaries may be to identify the top control point. To identify the top control point, an intensity projection may be computed in the vertical direction for an upper sub-region of the body region. In an embodiment, the upper sub-region comprises the uppermost one-third of the original image, e.g., one-third of the rows positioned at the top of the image. FIG. 8 illustrates a cropped radiographic image 800 corresponding to the uppermost one-third of the radiographic image 604. FIG. 9 illustrates a graph 900 of a smoothed vertical intensity projection vector corresponding to the cropped radiographic image 800. The graph 900 shows a local maximum value 911 of the projection smoothed vertical intensity projection vector.

Figure 11:
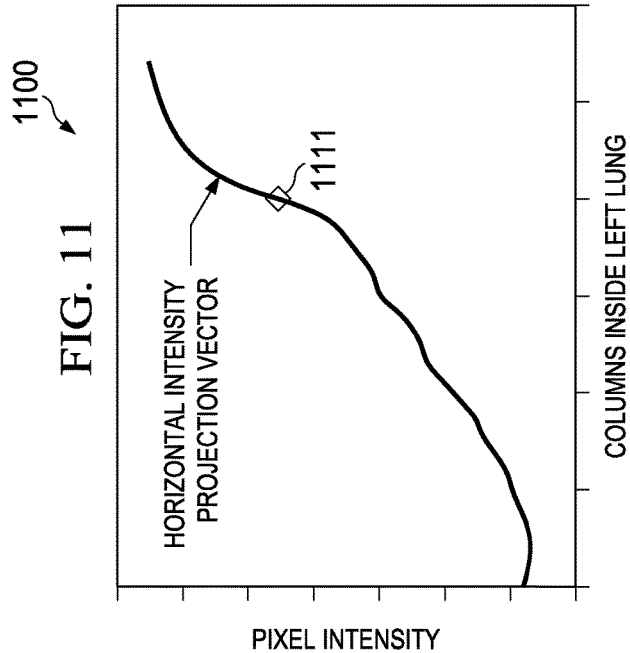
FIG. 11 illustrates a graph of another smoothed horizontal intensity projection vector.
Figure 10:
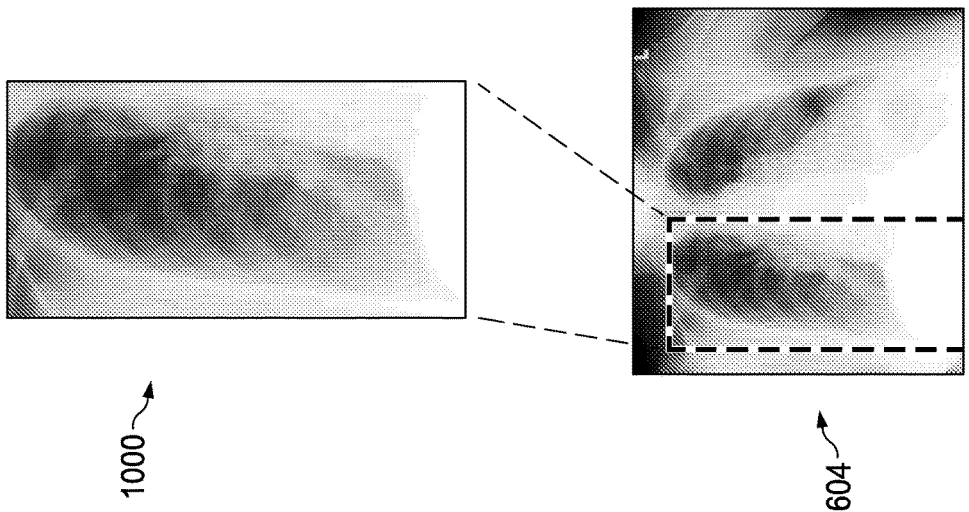
FIG. 10 illustrates a diagram of yet another embodiment radiographic image.

The next step in identifying ROI boundaries may be to identify the bottom control points for the right and left lungs, which are referred to as lower-right ROI boundaries and lower-left ROI boundaries. The lower-right ROI boundary may be identified in a right sub-region of the body region, which may comprise a portion of the body region below the upper ROI boundary and between the center ROI boundary and the right ROI boundary. For example, the bottom control point for the patient's right lung may be obtained by using the top, left, and mid control points to crop the radiographic image, computing a second derivative of a horizontal intensity projection for the cropped image, and computing a bottom control point in accordance with a last local maximum of the computed horizontal intensity projection. FIG. 10 illustrates a cropped radiographic image 1000 that results from using the top, left, right and mid control points to crop the radiographic image 604. FIG. 11 illustrates a graph 1100 of a smoothed horizontal intensity projection vector corresponding to the cropped radiographic image 1000. The graph 1100 shows a local maximum value 1111 of the projection smoothed horizontal intensity projection vector. The lower-left ROI boundary may be identified in a left sub-region of the body region, which may comprise a portion of the body region below the upper ROI boundary and between the center ROI boundary and the left ROI boundary. For example, the bottom control point for the patient's left lung may be identified using the top, right, and mid control points to crop the original image, computing a second derivative of a horizontal intensity projection for the cropped image, and computing a bottom control point in accordance with a last local maximum of the computed horizontal intensity projection.

Figure 12A:
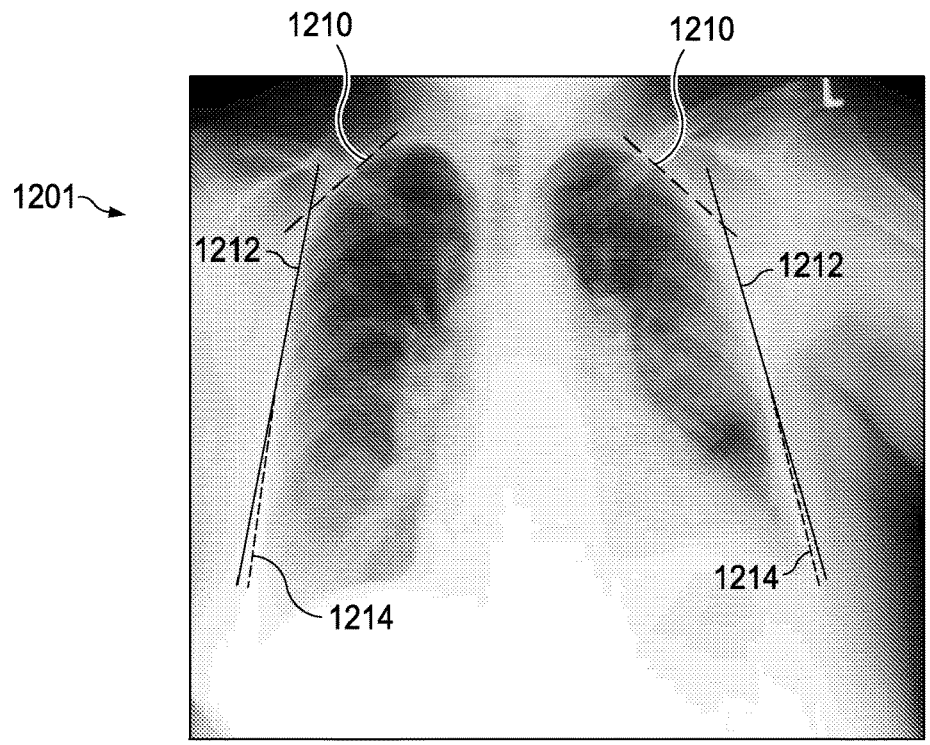
FIGS. 12A-12B illustrate diagrams of yet additional embodiment radiographic images.
Figure 12B:
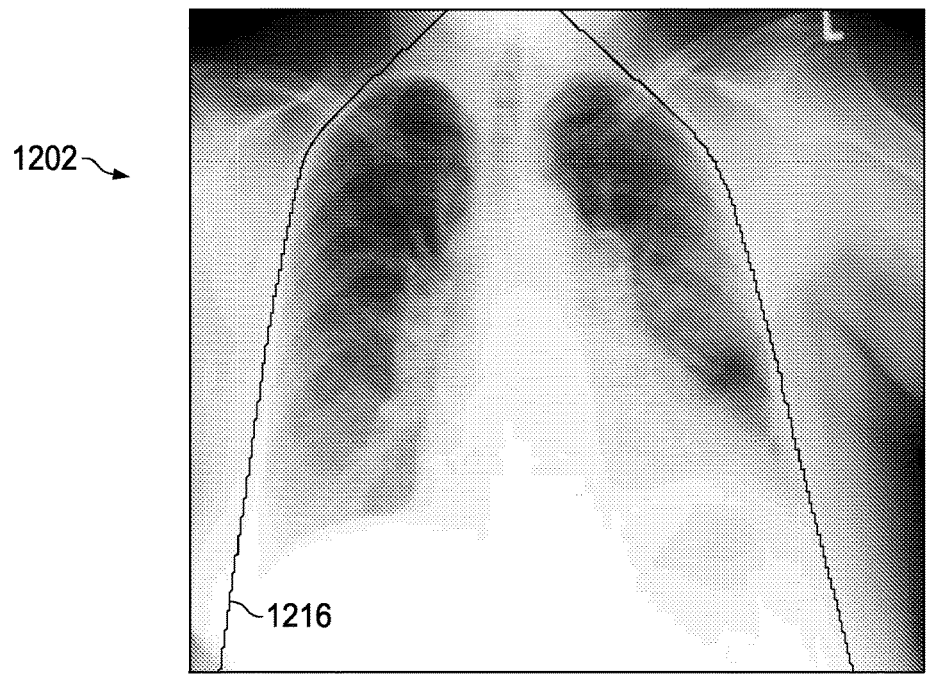

The outer lung boundary can be identified once the region of interest is found. The outer lung boundary is divided into three parts: a middle border; an upper border; and a lower border. FIG. 12A illustrates a radiographic image 1200 demonstrating a coarse estimation of the outer lung boundary, and FIG. 12B illustrates the outer lung boundary 1216. The coarse estimation of the outer lung boundary may produce an upper border 1210 (long dashed lines), a middle border 1212 (solid lines), and a lower border 1214 (short-dashed lines). The middle border 1212 can be estimated via a line-fitting procedure on outer-lung regions, which may be established using control points (e.g., ROI boundaries) and a lung center. Notably, outer-lung regions may comprise a region that is a threshold horizontal distance from the ROI boundary. The threshold distance may be calculated using coordinates of the ROI boundary and the lung center for each lung. Lines at varying orientations are fit to the second derivative of the established region, and the best fit line is selected as the middle border 1212 for the outer lung boundary. The upper border 1210 may be established using a line fitting procedure for a lower-lung region defined by the top control points and the middle border 1212. The lower border 1214 may be established using a line fitting procedure for a lower-lung region defined by the bottom half of middle border 1212. The upper border 1210, the middle border 1212, and the lower border 1214 can then be merged to form the outer-lung boundary 1216, as shown in FIG. 12B. One technique for merging the upper border 1210, the middle border 1212, and the lower border 1214 is to apply a Gaussian least squares fit algorithm to rows of the coarse estimation of the outer lung boundary.

Figure 13:
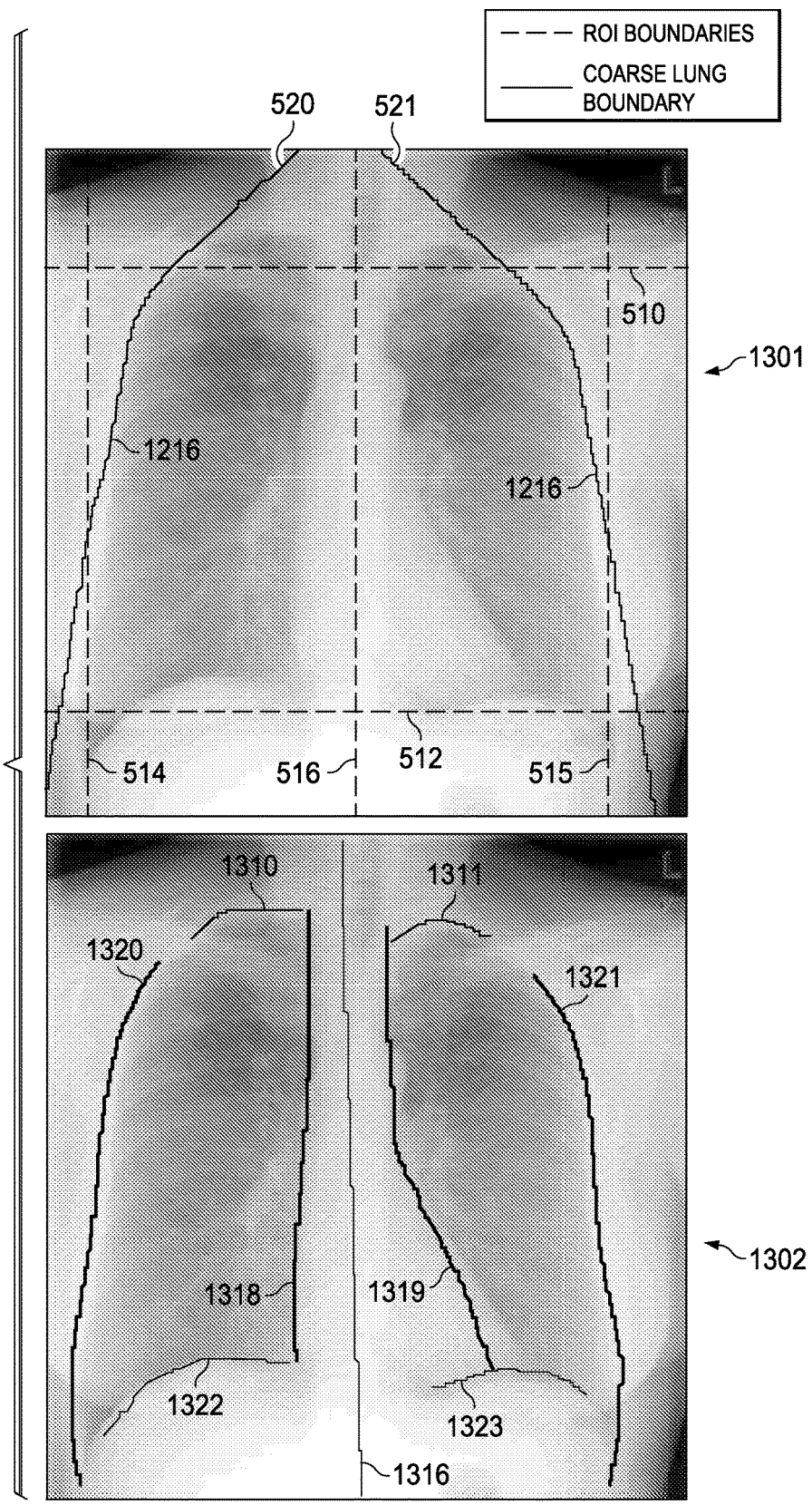
FIG. 13 illustrates diagrams of yet additional embodiment radiographic images.

Lung contours can be initialized after the outer lung boundary and region of interest are identified. FIG. 13 illustrates radiographic images 1301, 1302. The radiographic image 1301 includes the ROI borders 510-516 and the lung boundaries 1216. Lung boundaries can be generated from the ROI border and image features used to initialize lung boundaries. The radiographic image 1302 includes initial lung boundaries 1310-1321. As shown, the initial lung boundaries 1310-1321 are split into top, bottom, outer and inner borders, which may be initialized at a relatively coarse scale. The midline 1316 may be obtained by computing zero crossing points calculated from a first derivative of the image at a higher scale, and fitting a straight line to a subset of the zero crossing points that are closest to the mid control point. The zero crossing points may be computed in the horizontal direction.

Next, the zero crossing points calculated from the second derivative of the image in the horizontal direction are computed. Those of ordinary skill in the art will appreciate that derivatives (e.g., a second derivative) computed in a direction (or long a vector) may be a directional derivative (e.g., a second directional derivative). FIG. 14A illustrates a zero crossing points diagram 1401 depicting zero crossing points for the radiographic image 1301. Edge candidates that lie in the inner half of the midline 1420 and the right ROI boundary 1410, and the left ROI boundary 1430 are eliminated to obtain the zero crossing points diagram 1402 depicted in FIG. 14B. Thus, edge candidates include horizontal zero crossing points that are positioned closer to either the right ROI boundary 1410 or the left ROI boundary 1430 than the midline 1420. The outer lung boundary is selected as the set of edge candidates that has the closest distance to (e.g., are within a threshold distance of) their respective rough lung boundaries 1440, 1450, and the final lung outer lung boundary candidates 1460, 1470 are estimated as shown by the diagram 1403 depicted in FIG. 14C.

Next, the initial inner lung boundary is identified. To identify the initial inner lung boundary, zero crossing points calculated from the second derivative of the image are computed in the horizontal direction for the right lung and angled zero crossing points are computed for the left lung. The angled zero crossing points may be computed at an angle between a horizontal plane and a vertical plane, e.g., an angle of forty-five degrees, etc. FIG. 15A shows the zero crossing points at forty-five degrees. An initial mask 1520 is computed using the first derivative of a left inner-lung sub-region (e.g., at a higher scale) as shown in FIG. 15B. The left inner-lung sub-region may be a region depicting an inner-half of the left lung, e.g., a region halfway between the left ROI boundary and the midline.

The connected edge pixels inside the mask are combined in order to generate the initial left inner lung boundary 1530 as shown in FIG. 15C. A similar approach may be employed to detect the right inner boundary. For example, the right inner lung boundary may be formed by computing a right mask region in accordance with a first derivative of a right inner-lung sub-region, and identifying horizontal zero crossing points within the right mask region as right edge pixels, and performing line-fitting on the right edge pixels to form the right inner lung boundary.

Figure 16C:
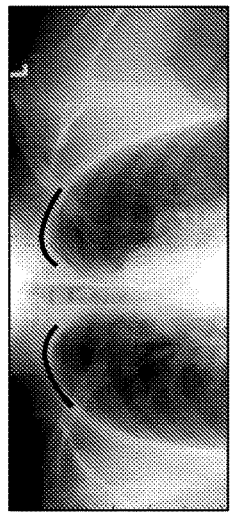
FIGS. 16A-16C illustrate diagrams of yet additional embodiment radiographic images.
Figure 16B:
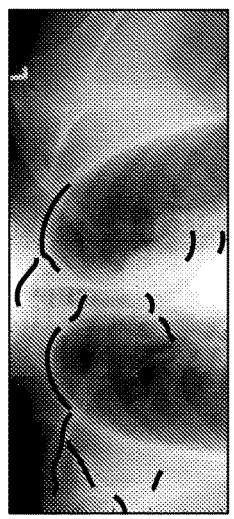
Figure 16A:
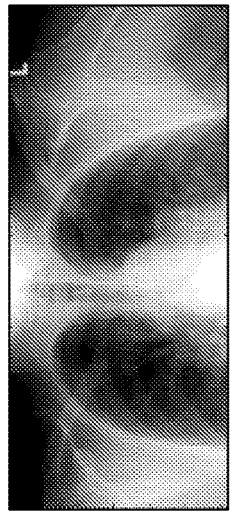

Thereafter, the initial top boundary is identified. The initial top lung boundary is selected as the set of edge candidates located at the top portion of the lung (e.g., within a threshold distance of the upper ROI boundary) and having a concave down structure. In addition, the length and angle of the concave down structure is considered in order to pick the appropriate top lung boundary. FIG. 16A illustrates a radiographic image 1601, and FIG. 16B illustrates a radiographic image 1602 depicting potential edge candidates for the radiographic image 1601. FIG. 16C illustrates a radiographic image 1603 depicting initial top lung boundary selected from the potential edge candidates depicted in the radiographic image 1602.

Figure 17B:
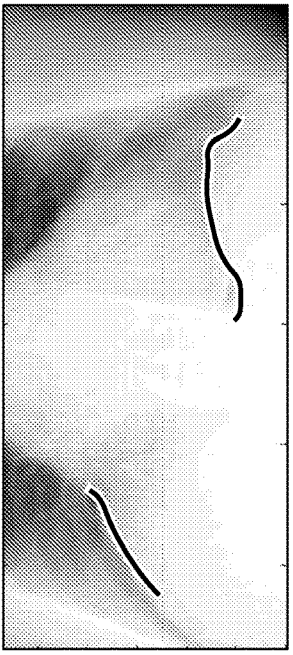
FIGS. 17A-17B illustrate diagrams of yet additional embodiment radiographic images.
Figure 17A:
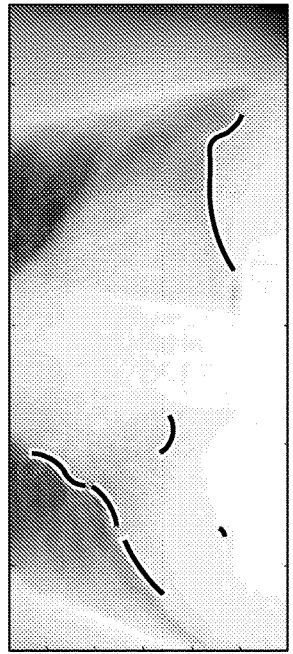

Next, the initial lower lung boundary (or bottom lung boundary) is identified. The initial lower lung boundary may be selected as a set of edge candidates located at the bottom portion of the lung (e.g., within a threshold distance of the lower ROI boundaries) and having a concave down structure. In addition, a width threshold and a second derivative magnitude threshold are used to ultimately select the lung boundaries from the edge candidates. FIG. 17A illustrates a radiographic image 1701 depicting potential edge candidates for the bottom portion of the lung depicted in the radiographic image 1601. FIG. 17B illustrates a radiographic image 1702 depicting the selected bottom lung boundaries.

Upon being initialized, the lung contours/boundaries may be refined. In some embodiments, the top, bottom, right and left initializations are refined individually, before being merged to produce the final lung segmentation output.

Figure 18A:
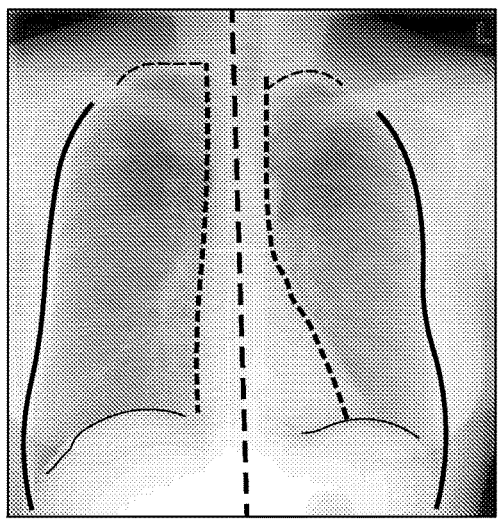
FIGS. 18A-18C illustrate diagrams of yet additional embodiment radiographic images.
Figure 18B:
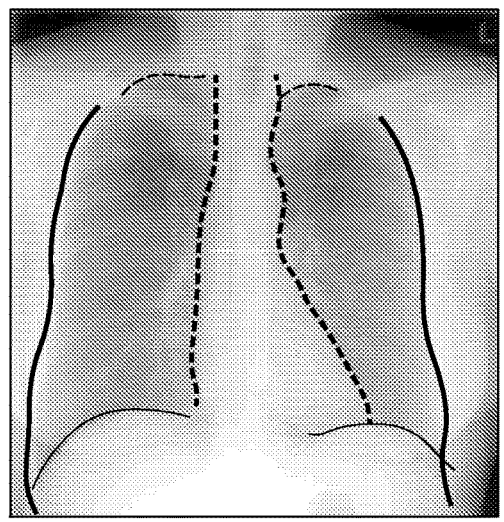
Figure 18C:
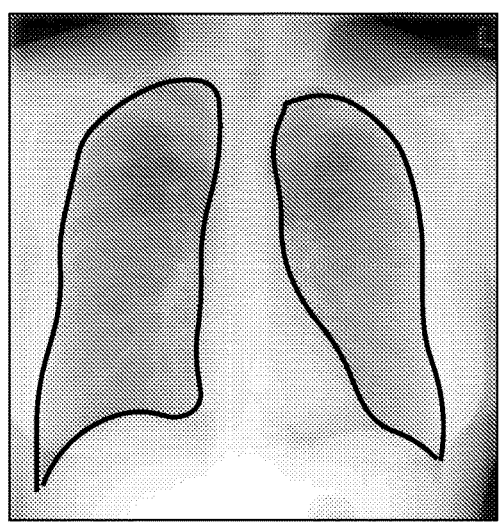

Lung contour refinement may begin with refinement of the outer lung boundary. For each point on the initial outer lung boundary, an intensity profile of a defined width is constructed in the normal direction. A search is performed on this intensity profile in order to identify the closest inner lung edge. All the points corresponding to the initial outer lung points are refined such that they correspond to the inner lung boundary. FIG. 18A illustrates a radiographic image 1801 depicting initialized lung boundaries. FIG. 18B illustrates a radiographic image 1802 depicting refined lung boundaries. FIG. 18C illustrates a radiographic image 1803 depicting a merged lung segmentation.

Figure 19A:
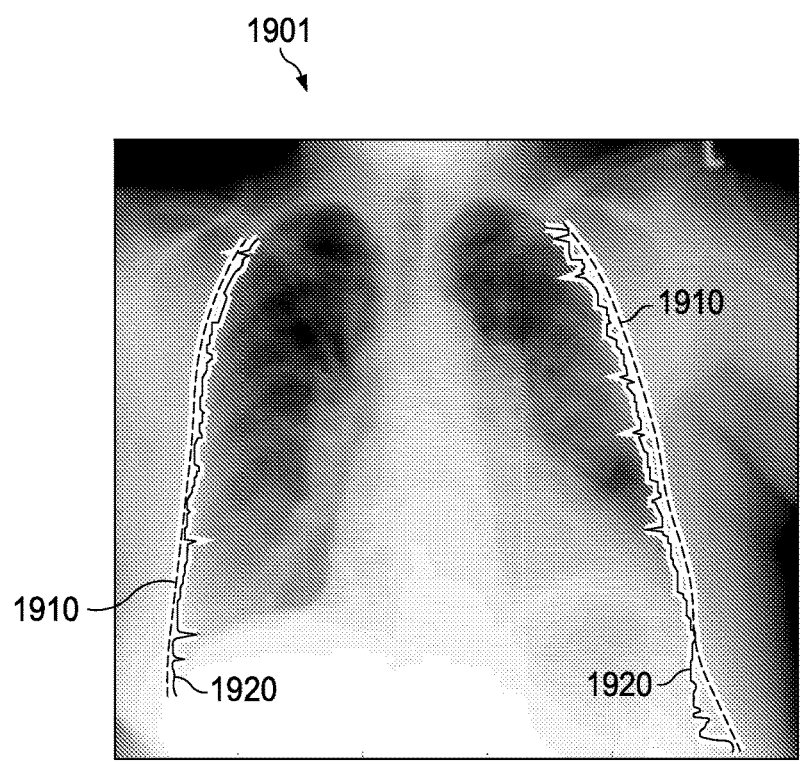
FIGS. 19A-19B illustrate diagrams of yet additional embodiment radiographic images.
Figure 19B:
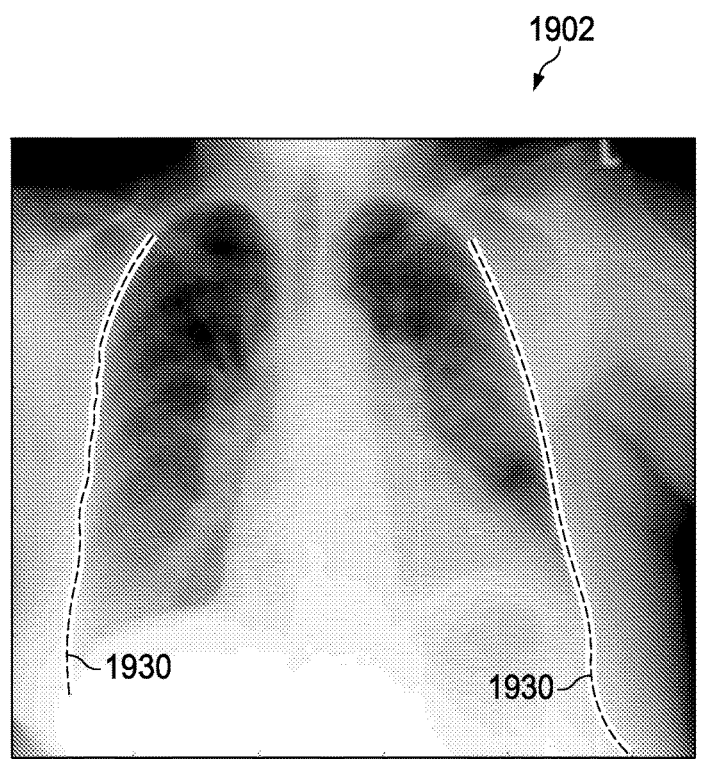

FIG. 19A illustrates a radiographic image 1901 depicting an initial outer lung boundary 1910 and an adjusted outer lung boundary 1920. The initial outer boundary 1910 may be adjusted based on closest inner edge on the intensity profile to obtain the adjusted outer lung boundary 1920. The adjusted outer lung boundary 1920 is then smoothed to obtain the final refined outer lung boundary 1930, as depicted by the radiographic image 1902 illustrated in FIG. 19B.

Figure 20A:
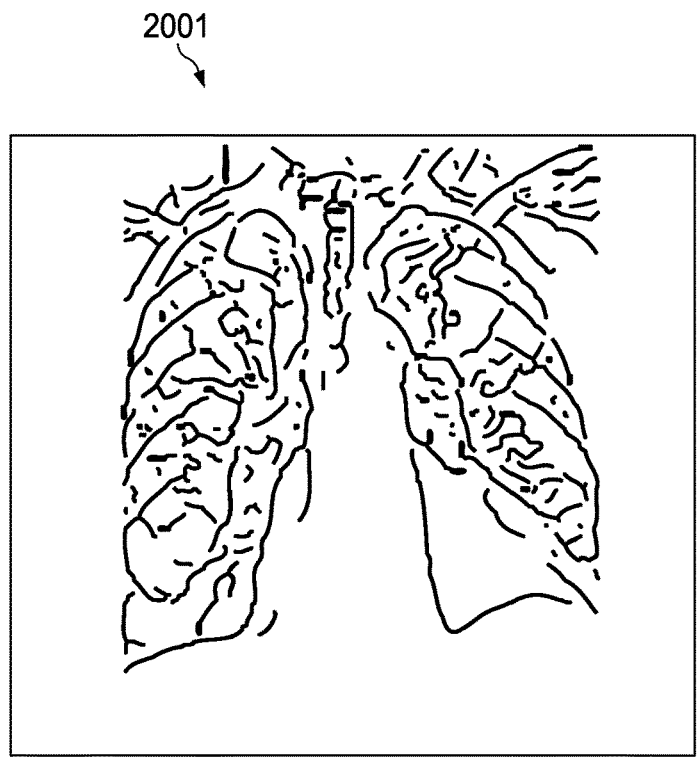
FIG. 20A illustrates a diagram of potential edge candidates for an inner lung boundary.
Figure 20B:
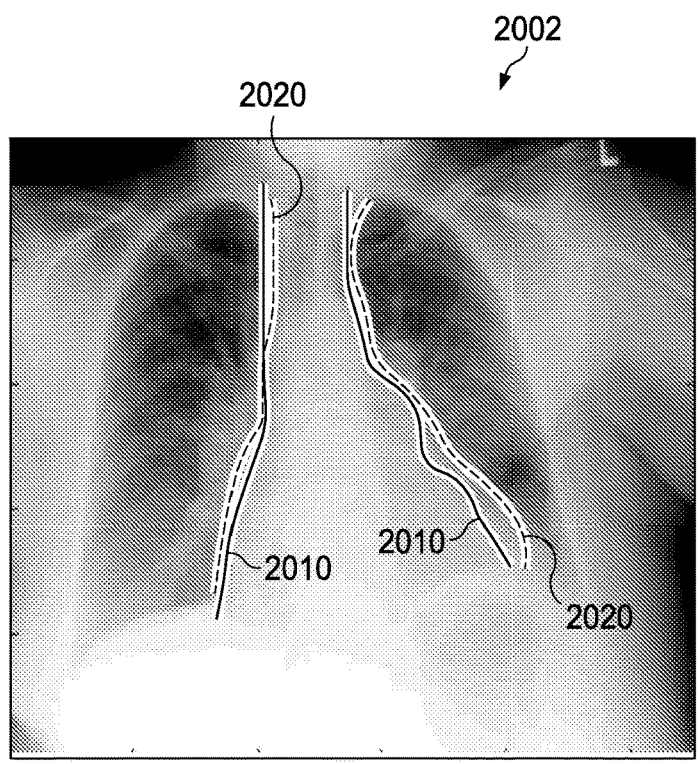
FIG. 20B illustrates a diagram of yet another embodiment radiographic image.

Embodiment lung contour refinement techniques may then proceed with refinement of the inner lung boundary. FIG. 20A illustrates a diagram 2001 of potential edge candidates for the inner lung boundary. In some embodiments, a canny edge detector is employed at multiple scales in order to detect the potential edge candidates for the inner lung boundary. FIG. 20B illustrates a radiographic image 2002 depicting an initial inner lung edge 2010 and a refined inner lung boundary 2020 lung boundary. In some embodiments the refined inner lung boundary 2020 is obtained by selecting edge candidates that are closest to the initial inner lung edge 2010 and have the strongest second derivative value.

Figure 21A:
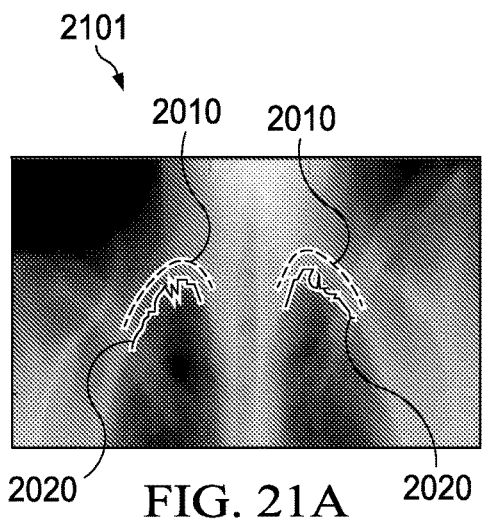
FIGS. 21A-21B illustrate diagrams of yet additional embodiment radiographic images.
Figure 21B:
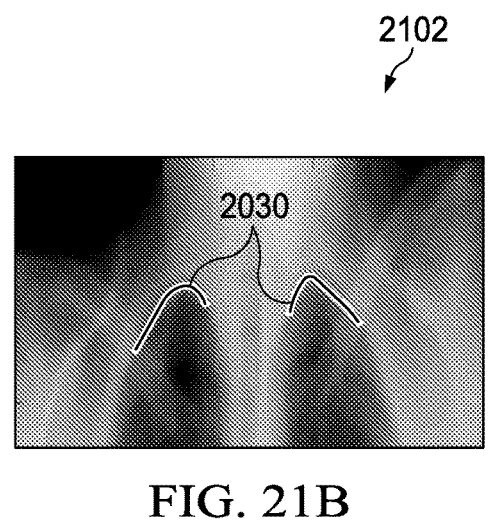
Figure 22A:
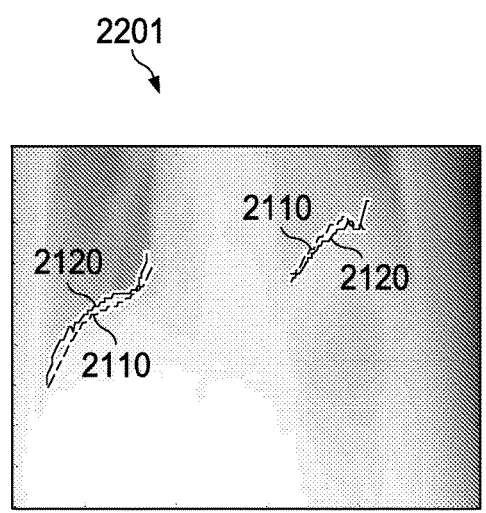
FIGS. 22A-22B illustrate diagrams of yet additional embodiment radiographic images.
Figure 22B:
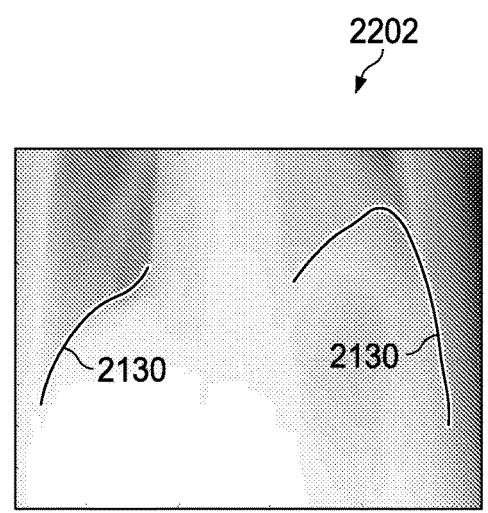

Subsequently, lung contour refinement may proceed to refine the top and bottom lung boundaries. The procedure used to refine the outer lung boundary may also be used to refine the upper and lower boundaries. FIG. 21A illustrates a radiographic image 2101 depicting an initial upper lung boundary 2110 and a refined upper lung boundary 2120. FIG. 21B illustrates a radiographic image 2102 depicting a smoothed upper lung boundary 2130. FIG. 22A illustrates a radiographic image 2201 depicting an initial lower lung boundary 2210 and a refined lower lung boundary 2220. FIG. 22B illustrates a radiographic image 2202 depicting a smoothed lower lung boundary 2230. In addition to smoothing, the left bottom lung boundary may also be extended up to the maximum column value of the refined left outer lung boundary. Once the lung boundaries are refined, the refined boundaries are merged to generate a lung segmentation result.

Figure 23:
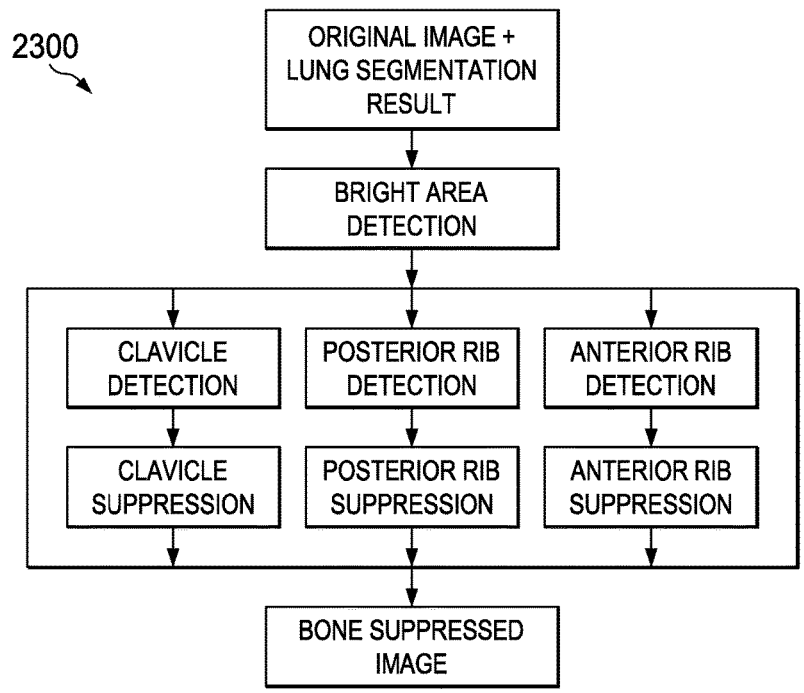
FIG. 23 illustrates a diagram of an embodiment bone suppression module.

In some embodiments, bone suppression may be performed after lung segmentation. FIG. 23 illustrates a diagram of a bone suppression module 2300 comprising bone detection and suppression stages. Embodiment bone suppression techniques may detect bright objects and devices, and then detect and suppress the clavicle, posterior and anterior ribs in the radiographic image.

Figure 24C:
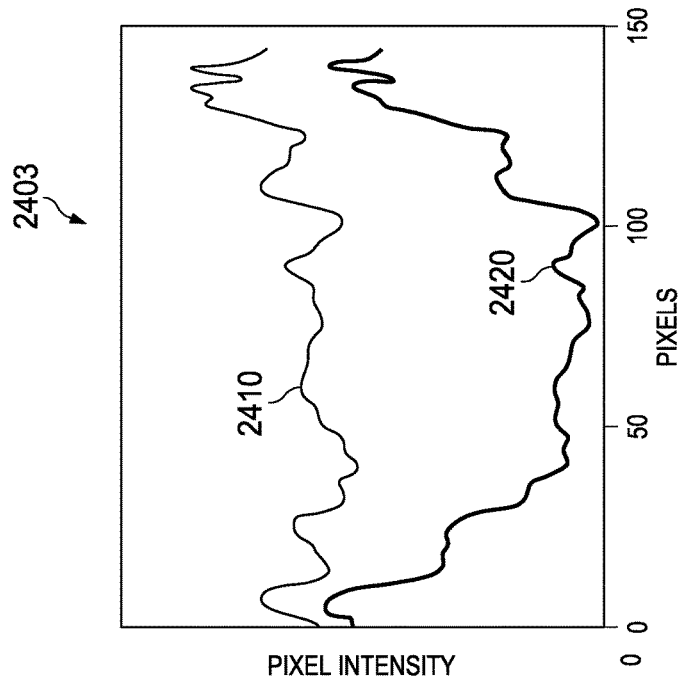
FIG. 24C illustrates a graph of radiographic image profiles.
Figure 24B:
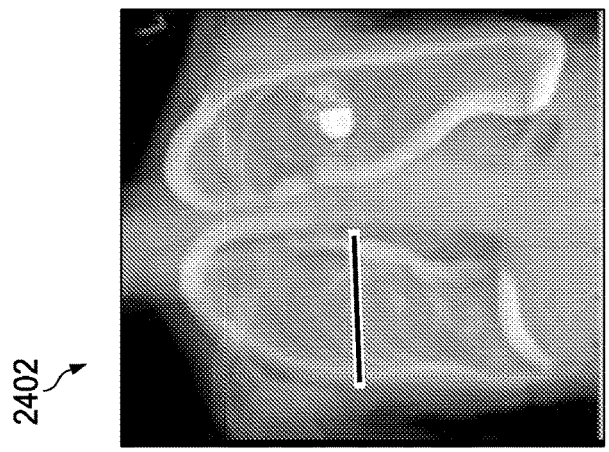
FIGS. 24A-24B illustrate diagrams of yet additional embodiment radiographic images.
Figure 24A:
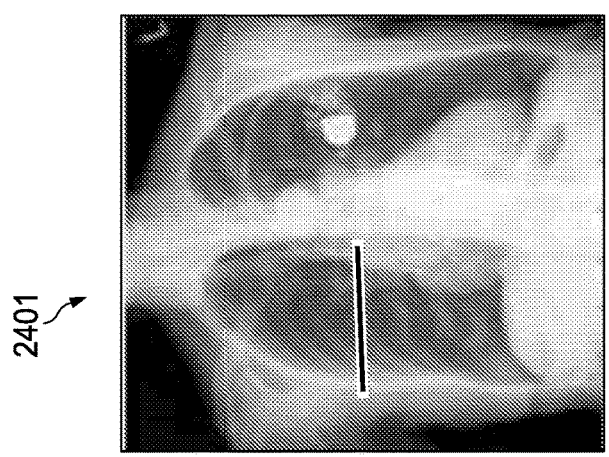

Embodiment bone suppression techniques may begin by extracting devices and bright objects so that they are not suppressed Extracting bright objects may avoid errors during bone signal estimation. Specifically, artificial objects may create artifacts having steep edges, which may interfere with bone signal estimation by, for example, masking abnormal lesions (e.g., lung cancers), or otherwise causing abnormal lesions to be suppressed. Devices may include high contrast medical devices (e.g., pacemakers, catheters, markers, etc.), while bright objects may include lobules, nodules, and other objects. Embodiment bone suppression techniques may then remove the lung background trend. For example, the lung background trend can be removed by fitting a polynomial (e.g., second order or higher) to the lung surface, and then subtracting the fit surface from the original image. FIG. 24A illustrates a radiographic image 2401 prior to removal of lung profiles. FIG. 24B illustrates a radiographic image 2402 after removal of the lung profiles. FIG. 24C illustrates a graph 2403 depicting a profile 2410 of the radiographic image 2401 prior to lung profile removal, and a profile 2420 of the radiographic image 2402 after lung profile removal.

Figure 25C:
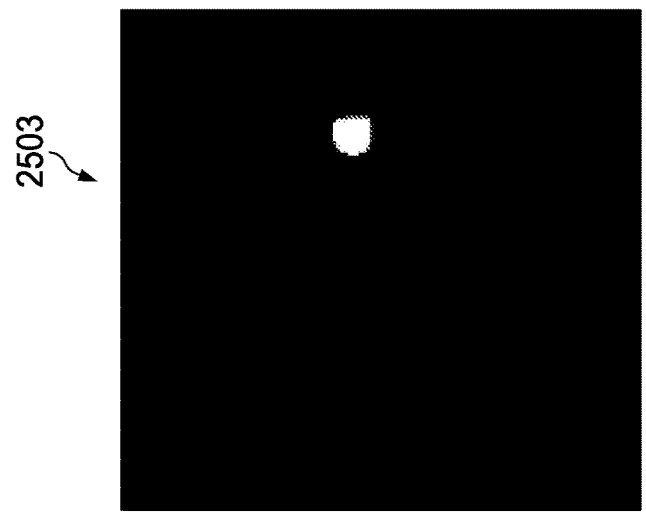
FIGS. 25A-25C illustrate diagrams of intensity profile locations in radiographic images.
Figure 25B:
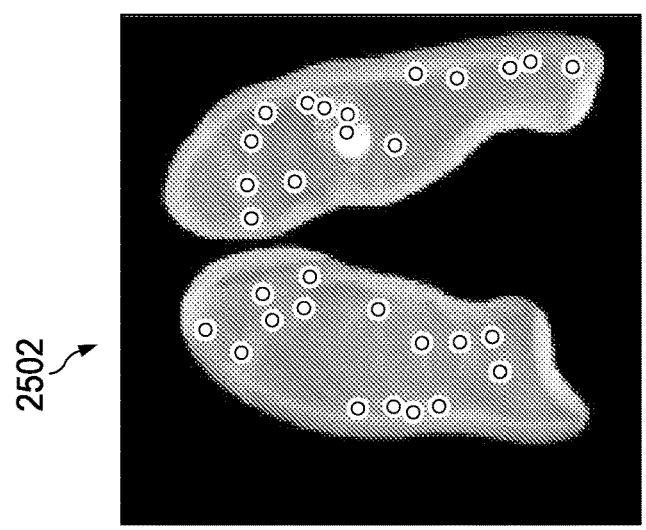
Figure 25A:
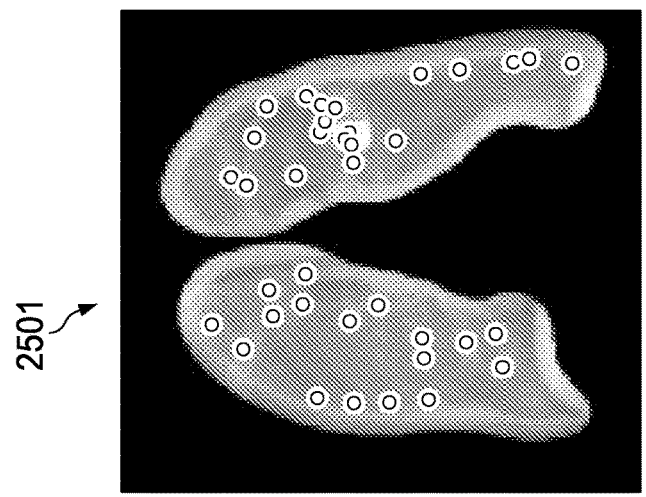

Once the lung profile is removed, embodiment bone suppression techniques may find high contrast areas. FIG. 25A illustrates a radiographic image 2501 depicting peaks (circles). The peaks and their corresponding contrasts are extracted from the previously computed image. A region growing technique is used to update the computed peaks, as shown in the radiographic image 2502 depicted in FIG. 25B. FIG. 25C illustrates a diagram 2503 of a bright region selected using features such as width, area, circularity and contrast of the object at multiple scales.

Aspects of this disclosure provide techniques for detecting clavicles, which may generally be the most prominent bones inside the lung region.

Some embodiment clavicle detection techniques may warp the radiographic image to obtain a warped radiographic image that depicts straighter clavical bones, e.g., the clavicle bones are depicted with less curvature in the warped radiographic image than in the original radiographic image. The clavicle detection techniques may then perform edge detection in the warped radiographic image to detect the clavicle bones.

Some embodiment clavicle detection techniques may warp the radiographic image iteratively to improve the accuracy of the clavical detection. For example, embodiment clavicle detection techniques may generate an angle map from clavicle bones in the radiographic image, and warp the radiographic image in accordance with the angle map to obtain a first warped radiographic image. The clavicle bones may be depicted with less curvature in the first warped radiographic image than in the radiographic image. The embodiment clavicle detection techniques may then update the angle map in accordance with the clavicle bones depicted in the first warped radiographic image, and re-warp the radiographic image in accordance with the updated angle map to obtain a second warped radiographic image that depicts the clavicle bones with less curvature than the first warped radiographic image. The embodiment clavicle detection techniques may then perform edge detection in the second warped radiographic image to detect the clavicle bones. In some embodiments, additional iterations of image warping may be performed to further increase the accuracy of clavicle bone detection.

Yet other embodiment clavicle detection techniques may create an apriori angle map by marking the clavical top and bottom edges over a training dataset, and obtaining angle measurements from the marked edges. The angles are then interpolated and low pass filtered to generate the apriori angle map. The embodiment clavicle detection techniques may then warp the image using the apriori angle map. Warping may be achieved by sampling the image along the contours that follow the angle map to obtain an image in which the clavicles are substantially horizontal. Next, the angle map may be updated by first performing edge detection using constraints associated with the angles, and then filtering the angle measurements to generate the updated image for the apriori angle map. The updated image is then warped back to the image space, and added to the apriori angle map so that the clavicles may be detected. To detect the clavicles, each lung is warped using the updated angle map to obtain an updated image in which the clavicles are substantially more horizontal than in the original image. Edge detection is then performed over the resulting image using various constraints to limit valid edge segments. Various edge segments are then joined to form edge candidates for the clavicle. Clavicle edge candidates on either side are then matched to select the best pair of clavicles that satisfy various constraints. Once detected, the clavicles can be suppressed using a technique that is similar to that used to suppress the posterior ribs, which is described in greater detail below.

Aspects of this disclosure provide techniques for detecting ribs, including anterior and posterior ribs. An embodiment rib detection technique generates an angle map for each rib in the radiographic image, and warps portions of the radiographic image depicting the ribs in accordance with the corresponding angle map to obtain a plurality of warped sub-images. The warped sub-images depict the ribs with less curvature than the radiographic image. The rib detection techniques may then detect the ribs by performing edge detection on the warped sub-images.

Aspects of this disclosure provide techniques for detecting and suppressing posterior ribs. In an embodiment, the posterior ribs are first warped using a case-specific angle map to straighten the posterior ribs, and then the ribs are detected using an approximate rib location technique. More specifically, an angle map is computed for each rib using the following procedure. First, the procedure generates angle measurements in real space. This may be achieved by performing a low pass filtering operation over the image, and then performing edge detection and threshold filtering. A grid consisting of a number of points made up of rows and columns (e.g., forty points made up of eight rows and five columns) is formed and angle measurements for the nearest points on detected edges are computed. Thereafter, the angle measurements are subjected to constraints based on an apriori angle map, and angle measurements outside the range (e.g., as defined by the apriori angle map) are eliminated such that only those measurements that satisfy the constraints are retained. Thereafter, an angle map for each lung is created from the retained angle measurements using an interpolation technique. The image is then sampled along contours that follow the angle map, thereby obtaining an image in which the ribs are substantially horizontal. Angle measurements are again computed using embodiment techniques provided by this disclosure, and the measurements are once again subjected to constraints to obtain valid angle measurements. The valid angle measurements are then added to the angle map, and the result is filtered to create a smooth angle map.

After obtaining the smooth angle map, the angle map is modified such that the angles around the outer lung edges follow the closest lung boundary. Thereafter, approximate rib locations are estimated using an embodiment approximation technique. The embodiment approximation technique may begin by warping the image based on angle maps such that the image is sampled along contours that follow the angle map, thereby obtaining a resulting image in which the ribs are substantially horizontal. The embodiment approximation technique may then smooth the image at several scales to find structures of different sizes, and obtain measurements from the identified structures. The measurements may have various classifications. For example, the measurements may be associated with the top edge, the bottom edge, the ridge, or the valleys of the rib structure. Measurements associated with the top and bottom edges may be obtained by finding the local maxima of image gradients in the direction of the gradient. Measurements associated with the ridges and valleys may be obtained by finding the local extrema (e.g., maxima and/or minima) of the concavity in the image.

Thereafter, the embodiment approximation technique may accumulate the obtained measurements according to the location of those measurements to obtain a final accumulation image having higher values at rib location than at locations where there is no rib. Each measurement may be spread out vertically to account for location error, and then shifted according to classification/type. For example, measurements associated with the top edges may be shifted down one-half rib-width, while measurements associated with bottom edges may be shifted up one-half rib-width. In some embodiments, measurements associated with ridges and valleys are not shifted. Each measurement's contribution may be weighted by type. In one example, measurement contributions associated with top/bottom edges are weighted more heavily than measurements associated with ridges or valleys. In some embodiments, measurements associated with valleys are assigned a negative weighting to indicate that a rib should not be there. The resulting accumulation image may have horizontal bands indicating the location of ribs. The horizontal bands may be segmented and the vertical position may be measured at several horizontal locations across the image.

Subsequently, the rib detections may be mapped into a rib cage coordinate system. A coordinate system may be created for each lung based on three lines, namely: a vertical line along the medial edge of the lung; a horizontal line just above the lung; and a lateral line along the lateral edge of the lung. The horizontal line may establish a reference for the vertical line and the lateral line. After creating the coordinate systems, the rib cage model may be extracted. The rib cage coordinate system may provide a frame work for locating ribs in the rib cage. The rib cage model may match points along the medial side of the lung to points along the anterior side of the lung. These points may be initially matched using the angle map, after which the locations of matching points may be adjusted to better fit the rib location measurements. The points may be constrained to maintain consistent distances between ribs. Once the location of matching points is determined, the rib distances may be examined to filter out measurements that are inconsistent with the rib cage, as well as to infer the existence of ribs that were not directly detected.

Precise rib locations may then be computed with the aid of the approximate rib locations computed previously. The approximate rib locations may reflect an estimate of the position of the center line of each rib, and may extend from the medial edge of the rib cage coordinate system to the lateral edge. A sub-image may then be created from the original image for each approximate rib location by sampling a non-uniformly spaced grid aligned with the approximate rib location. The central row of this grid may be created by sampling along the approximate rib location line in one pixel intervals. The rows above and below this central row may be created by marching out in one pixel increments from each point in the central row in the direction perpendicular to the rib. Rows are added to the grid until it extends above and below the central row by either the estimated spacing between ribs or two centimeters, whichever is greater. The resulting sub-images may each contain a single rib warped to be at least partially horizontally and vertically centered in relation to the radiographic image.

Thereafter, edge measurements may be gathered. To gather the edge measurements, the sub-images may first be smoothed using an asymmetric Gaussian technique to deemphasize their vertical structure. Edge points are then found by identifying local maxima in the gradient magnitude. Edge points may be filtered out if their gradient magnitude is below a threshold (e.g., the thirtieth percentile) or if their orientation along the edge is more than a threshold angle (e.g., thirty degrees) from horizontal. Remaining adjacent edge points of similar orientation may be connected into edge measurements. Measurements shorter than a minimum length requirement can be discarded and top and bottom edge measurements may be separated.

After being gathered, the edge measurements may be combined to generate candidate edge measurement combinations. In some embodiments, every combination of edge measurements is considered. Combinations that are inconsistent with representing a single rib based on spatial relationships between the edges are filtered out. For example, combinations where edges of the same type (e.g., top edges, bottom edges, etc.) overlap horizontally by more than a threshold length (e.g., one third of their length, etc.) are eliminated. As another example, combinations where edges of the same type have endpoints that are horizontally near one another are eliminated. As yet another example, combinations where top and bottom edge measurements overlap horizontally, but are either too far apart or too close together to represent the edges of a rib, are also eliminated. If the number of remaining combinations of edge measurements is greater than a threshold (e.g., 256, etc.), then the combinations containing the shortest remaining measurements are removed until the remaining combinations are less than or equal to the threshold.

Thereafter, embodiment techniques may build individual rib models. The rib models may be created from the remaining combinations of measurements. A rib model may be a contiguous path across the sub-image, and may be intended to estimate true edges of the rib bone that is the source of the corresponding combination of edge measurements. To create a smoothly varying path across the sub-image that follows the edge measurements for each combination, a Rauch-Tung-Striebel smoother is applied. The state space model for the smoother only tracks a rib center (row) position and width across image columns. The process variance is initialized to be very high to allow a reasonably tight fit to the edge measurements. Once rib models are computed, models that do not satisfy certain constraints are discarded. Models that do not satisfy constraints may include models with regions of high second derivative or models with widths more than a threshold distance from the approximate rib width.

Next, the rib models are ordered according to a coverage metric. The coverage metric may correspond to the number of columns in the sub-image, where a top or bottom edge measurement is included but not overlapped with another measurement of the same type. Models with higher coverage may be considered more reliable than those with lower coverage, since they tend to be more consistent with the detected edges. The model coordinates are then transformed back into the coordinate system of the original image, which may undo the transform that attempted to straighten the ribs in their individual sub-images. The result may be a polygon that outlines the candidate rib in the original image. An output of building the individual rib models may be a selected candidate rib and an ordered set of alternate candidate ribs for each rib approximation.

After building the individual ribs, the embodiment technique may select a globally consistent set of rib models. Select a globally consistent set of rib models may use information from all of the detected ribs to select a set of candidate ribs that offer a consistent interpretation of the ribs as a rib cage. To determine if a set of candidate ribs matches the expectations for a rib cage, a global model may be used with a set of constraints associated with the expectations. For example, the set of constraints in the global model may correspond to a linear, non-decreasing relationship between rib width and row position of a rib. The set of constraints may also correspond to a linear, non-decreasing relationship between inter-rib spacings, e.g., the spacing between a lower rib and an upper rib based on a row position of the upper rib. The model may maintain consistent constraints/relationships for the left and right lungs.

The quality of a given set of candidate ribs may be determined by measuring a difference between the candidate's parameters (e.g., rib spacing/width values) and the model's parameters. This may be achieved using a robust linear regression technique to obtain a quality metric, which may be a weighted mean squared error between the measured values and the linear models' predictions. The rib width and spacing models can be fit using the best candidate ribs. Using the model-predicted values for rib width, rib candidates for all ribs may be filtered to remove extreme outliers. If any of the best candidate ribs were removed and replaced with their best alternate rib, the rib width and spacing models are updated.

The amount of overlap (if any) between the polygons describing each best candidate rib and other nearby ribs are computed. If there is significant overlap between a pair of candidates, then each alternate rib for each member of the pair is individually substituted into the rib cage and the quality of the resulting set of candidates is recorded. After considering all the alternatives, the combination of candidates with the best quality score is recorded and used as the new set of best candidates. If these substitution tests result in a change to the set of best candidate ribs, then the rib width and spacing models are updated accordingly. This process, where there is a test to identify an unlikely configuration of one or more ribs (above it was for overlap) followed by substitution of alternate candidate ribs and evaluation of the quality metric, may be repeated for other criteria. These include individual candidate rib width statistics and statistics computed over inter-rib spacing. The full set of tests can then be iterated until the set of best candidates is stable or until timing requirements limit further search. The search process ultimately provides a set of best candidates that specify precise rib locations. After identifying precise rib locations, the posterior ribs may be suppressed.

Aspects of this disclosure provide bone suppression techniques for removing/suppressing detected bones from radiographic images. The bones may be suppressed individually on a bone-by-bone basis. One embodiment bone suppression technique includes selecting one of the detected bones to suppress from the radiographic image, identifying a rectangular sub-image depicting the selected bone, and clipping edges of selected bone positioned outside a lung region from the rectangular sub-image. The embodiment technique further includes performing image processing on the rectangular sub-image to reduce a curvature of the selected bone, estimating a bone profile from the processed rectangular sub-image, and suppressing the bone profile from the radiographic image. The bone profile may be estimated by removing a background signal from the processed rectangular sub-image to generate a background-removed image, identifying upper and lower edge profiles of the selected bone depicted by the background-removed image, and estimating the bone profile in accordance with the upper and lower edge profiles. Notably, a bone edge signal estimation may also be performed using the processed rectangular sub-image or the background-removed image. Estimation of the bone edge signal may be performed separately from estimation of the bone signal (e.g., bone profile), as the bone edge may have a relatively higher contrast than other parts of the bone. In an embodiment, the bone edge signal estimation is performed on a directional subsampled sub-image, which is obtained by subsampling an image (e.g., the processed rectangular sub-image) at a higher frequency in a direction that is parallel to the bone than in a direction that is perpendicular to the bone. The bone edge signal estimation may further include morphological processing (e.g., min-max processing) and image smoothing (e.g., Gaussian smoothing) to reduce the likelihood of removing structures other than bones, like abnormal diseases and other normal structures, e.g., blood vessels, etc. For instance, the directional subsampled sub-image may be morphologically processed to obtain a processed directional subsampled sub-image. The processed directional subsampled sub-image may then be smoothed to obtain a smoothed directional subsampled sub-image. During smoothing, a smaller sigma value may be used to smooth regions near the bone edge. The sigma value corresponds to the variance of the low-pass filter, and consequently using a smaller sigma value (e.g., tighter variance) near the bone edge may provide a more accurate approximation of the bone edge signal, e.g., sharper edge.

Aspects of this disclosure further provide rib suppression techniques. Embodiment rib suppression techniques may be carried out sequentially on each rib in both lungs. The top or bottom most rib may be suppressed and the output image with that rib removed may be passed as an input for removal of the next rib (e.g., the rib above or below the rib being removed). This can be repeated until all ribs are suppressed. The input image for the rib that is being suppressed at any time is the image with all the previous ribs removed. The process can be performed from top to bottom, or vice versa. Rib suppression for the left and the right lungs may be performed independently.

A first step of embodiment posterior rib suppression techniques may be to create a rib sub-image. As an example, the rib sub-image may be a rectangular sub-image around the bone being suppressed, which may be cropped from the full resolution image. This may reduce processing time, since rib suppression is generally performed one rib at a time. After creating the rib sub-image, the embodiment posterior rib suppression techniques may proceed to refine the rib edges. Since rib detection is typically performed on a subsampled image, refinement at the original image resolution may avoid introducing artifacts during the suppression process. This refinement is carried out by computing intensity profiles vertical to rib edges at each point, and then refining the edges based on the first derivative along the vertical profiles. These refined rib edges are then smoothed in order to remove any discontinuities that may have been introduced due to noise. FIG. 26 illustrates a radiographic image 2600 of a detected rib in which the detected rib edges 2610 and refined rib edges 2620 are shown. After refining the rib edges, embodiment techniques may clip outside the lung area to remove areas of the rib that are not inside the lung area. Notably, clipping may reduce complexity for implementations that are primarily (or exclusively) interested in suppressing the part of the rib that lies inside the lung area. Due to this reason, rib edges at both ends are truncated to lie within the lung area. FIG. 27 illustrates a radiographic image 2700 in which the detected rib edges have been clipped outside the lung area. Thereafter, embodiment techniques may straighten the ribs. To achieve this, the upper and lower edges of the ribs are resampled, and a center line is constructed between the two resampled edges. Interpolated matrices of vertical and horizontal indices are then created normal to the center line, where each column of the matrices represent interpolated horizontal and vertical indices starting from a point on the upper rib edge and ending at a point on the lower rib edge. The matrices are then used to create a straightened (horizontal) rib image. FIG. 28 illustrates a radiographic image 2800 depicting a straightened rib.

After straightening the rib, a rib profile estimation may be performed to remove a background signal from the straightened rib image. This may be beneficial for estimating the true bone profile, as well as for preventing the background signal from being suppressed. Points above the upper edge and below the lower edge are used to interpolate a region between those points. Gaussian least squared fitting may be carried out over this interpolated region. Thereafter, the background image may be subtracted from the straightened rib image to remove the background image.

The upper and lower edges of the rib may have relatively high intensities compared to the rest of the rib. As such, the edge profiles may be estimated, and then subtracted from the background removed image in order to avoid introducing artifacts during the suppression process. A min-max operation can then be carried out over the image, after which smoothing may be performed in order to avoid remove abnormalities (nodules, etc.) and other structures. Subsequently, the edge profiles can be added back to the image, and the resulting image can be mapped back to the original image space. Thereafter, the rib profile estimation may be subtracted from the sub-image, and the sub-image may be substituted for the original cropped sub-image in the input image, thereby achieving a rib suppressed image. Suppression may be performed in a similar fashion for each of the remaining ribs.

Aspects of this disclosure provide techniques for anterior rib detection. Anterior rib detection may begin computing an angle map for each case by warping the anterior ribs using an apriori map in a fashion similar to that used to warp the posterior ribs. Thereafter, the image may be low-pass filtered, and an edge detection mechanism may be performed on the resulting low-pass filtered image to generate angle measurements. The angle measurements are then subjected to constraints to filter out measurements that are outside a valid angle range for the anterior ribs. The angle range may be computed by constructing the apriori angle map using a training set of images. Valid angle measurements are then interpolated and low pass filtered to form an update image. This image is then warped back to the real image space, and the resulting image is added to the apriori angle map which is then used to perform subsequent anterior rib detection operations.

Aspects of this disclosure provide techniques for approximating anterior rib locations. Techniques for locating the approximate rib locations for anterior ribs may be similar to those used to locate approximate rib locations for posterior ribs, except that the rib cage coordinate system for the anterior ribs may separate each lung into an upper region and a lower region. Anterior rib locations in the lower region may be approximated using techniques that are similar to those used to approximate the posterior rib locations. Anterior rib locations in the upper region may be approximated by matching locations between the medial line and the upper line using the intersection of those two lines as a reference point. Techniques for identifying precise rib locations for anterior ribs may be similar to those used to identify precise rib locations for posterior ribs.

Techniques for suppressing anterior ribs may be similar to those used to suppress posterior ribs. Anterior rib suppression may be restricted to the ribcage in order to avoid introducing artifacts at the lung edge. The smoothed image outside the lung mask is added back to the bone suppressed image inside the lung mask using the following equation: Out=Orig−SLM*(Orig−Bone Suppressed). FIG. 29A illustrates a radiographic image 2901, and FIG. 29B illustrates a radiographic image 2902 of a final bone suppressed image for the radiographic image 2901.

Nodule detection can be performed on the bone suppressed image. Nodule detection techniques may be similar to mass detection techniques described by U.S. patent application Ser. No. 13/695,369 filed on Oct. 30, 2012, entitled "Spiculated Malignant Mass Detection and Classification in Radiographic Images," which is incorporated by reference herein as if reproduced in its entirety.

Figure 30:
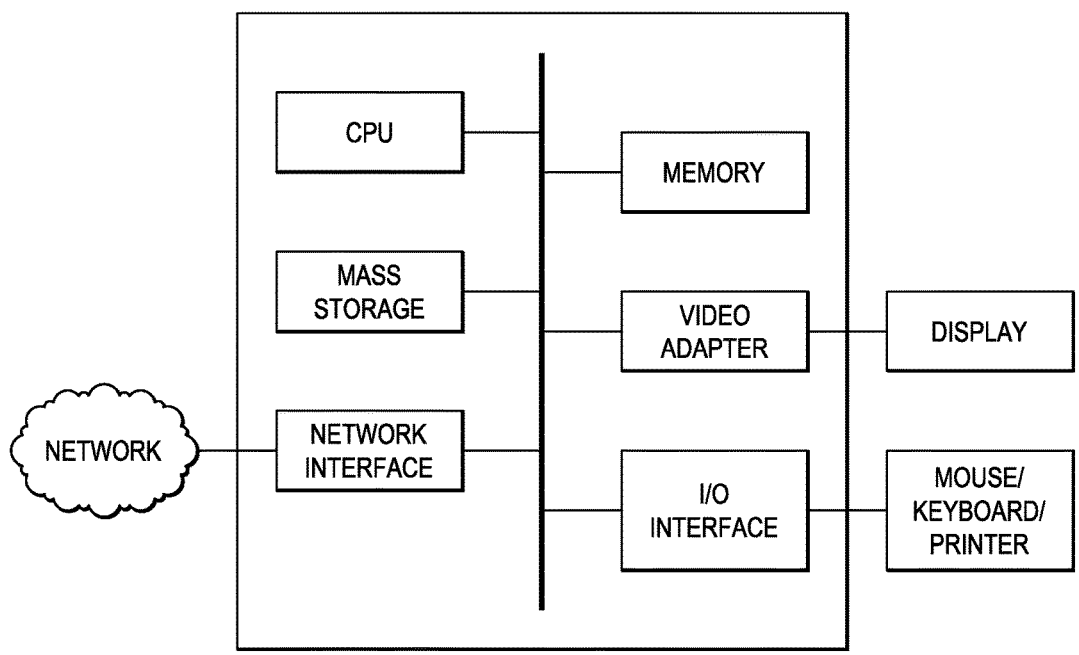
FIG. 30 illustrates a diagram of an embodiment computing platform.

FIG. 30 is a block diagram of a processing system that may be used for implementing the devices and methods disclosed herein. Specific devices may utilize all of the components shown, or only a subset of the components, and levels of integration may vary from device to device. Furthermore, a device may contain multiple instances of a component, such as multiple processing units, processors, memories, transmitters, receivers, etc. The processing system may comprise a processing unit equipped with one or more input/output devices, such as a speaker, microphone, mouse, touchscreen, keypad, keyboard, printer, display, and the like. The processing unit may include a central processing unit (CPU), memory, a mass storage device, a video adapter, and an I/O interface connected to a bus.

The bus may be one or more of any type of several bus architectures including a memory bus or memory controller, a peripheral bus, video bus, or the like. The CPU may comprise any type of electronic data processor. The memory may comprise any type of system memory such as static random access memory (SRAM), dynamic random access memory (DRAM), synchronous DRAM (SDRAM), read-only memory (ROM), a combination thereof, or the like. In an embodiment, the memory may include ROM for use at boot-up, and DRAM for program and data storage for use while executing programs.

The mass storage device may comprise any type of storage device configured to store data, programs, and other information and to make the data, programs, and other information accessible via the bus. The mass storage device may comprise, for example, one or more of a solid state drive, hard disk drive, a magnetic disk drive, an optical disk drive, or the like.

The video adapter and the I/O interface provide interfaces to couple external input and output devices to the processing unit. As illustrated, examples of input and output devices include the display coupled to the video adapter and the mouse/keyboard/printer coupled to the I/O interface. Other devices may be coupled to the processing unit, and additional or fewer interface cards may be utilized. For example, a serial interface such as Universal Serial Bus (USB) (not shown) may be used to provide an interface for a printer.

The processing unit also includes one or more network interfaces, which may comprise wired links, such as an Ethernet cable or the like, and/or wireless links to access nodes or different networks. The network interface allows the processing unit to communicate with remote units via the networks. For example, the network interface may provide wireless communication via one or more transmitters/transmit antennas and one or more receivers/receive antennas. In an embodiment, the processing unit is coupled to a local-area network or a wide-area network for data processing and communications with remote devices, such as other processing units, the Internet, remote storage facilities, or the like.

The following references are related to subject matter of the present application. Each of these references is hereby incorporated herein by reference in its entirety: U.S. patent application Ser. No. 13/808,229 filed on Jan. 3, 2013, entitled "Marking System for Computer-Aided Detection of Breast Abnormalities;" U.S. patent application Ser. No. 13/695,351 filed on Oct. 30, 2012, entitled "Probability Density Function Estimation;" U.S. patent application Ser. No. 13/695,347 filed on Oct. 30, 2012, entitled "Microcalcification Detection Classification in Radiographic Images;" U.S. patent application Ser. No. 13/168,614 filed on Jun. 24, 2011, entitled "Breast Skin Line Detection in Radiographic Images;" U.S. patent application Ser. No. 13/168,588 filed on Jun. 24, 2011, entitled "Breast Segmentation in Radiographic Images;" and U.S. patent application Ser. No. 10/996,595 filed on Nov. 23, 2004, entitled "CAD Medical Imaging System, Components, and Method of Operation."

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method for performing bone suppression, the method comprising:
  receiving a radiographic image;
  detecting bones in the radiographic image, the detected bones comprising one or a combination of a clavicle bone, a posterior rib bone, and an anterior rib bone;
  suppressing the detected bones in the radiographic image to generate a bone suppressed image; and
  filtering the radiographic image prior to detecting the bones in the radiographic images,
  wherein filtering the radiographic image includes removing high contrast medical devices from the radiographic image, and removing a lung background trend from the radiographic image.

2. The method of claim 1,
  wherein removing the lung background trend comprises:
    generating a fitted lung surface by fitting a polynomial to a lung surface in the radiographic image; and
    subtracting the fitted lung surface from the radiographic image.

3. The method of claim 1, wherein detecting the bones in the radiographic image comprises:
  warping the radiographic image to generate a warped radiographic image, wherein the clavicle bones are depicted with less curvature in the warped radiographic image than in the radiographic image; and
  performing edge detection in the warped radiographic image to detect the clavicle bones.

4. The method of claim 1, wherein detecting the bones in the radiographic image comprises:
  generating an angle map from clavicle bones in the radiographic image;
  warping the radiographic image in accordance with the angle map to generate a first warped radiographic image, wherein the clavicle bones are depicted with less curvature in the first warped radiographic image than in the radiographic image;
  updating the angle map in accordance with the clavicle bones depicted in the first warped radiographic image;
  re-warping the radiographic image in accordance with the updated angle map to generate a second warped radiographic image, wherein the clavicle bones are depicted with less curvature in the second warped radiographic image than in the first warped radiographic image; and
  performing edge detection in the second warped radiographic image to detect the clavicle bones, and
  wherein generating the angle map from the clavicle bones in the radiographic image comprises:
    marking the clavicle bones in the radiographic image using a training data set;
    generating angle measurements from the marked radiographic image; and
    interpolating the angle map from the angle measurements.

5. The method of claim 1, wherein detecting the bones in the radiographic image comprises:
  generating angle maps for ribs in the radiographic image, wherein a different one of the angle maps is generated for each of the ribs;
  warping portions of the radiographic image depicting the ribs in accordance with a corresponding one of the angle maps to generate a plurality of warped sub-images, wherein the ribs are depicted with less curvature in the plurality of warped sub-images than in the radiographic image; and
  performing edge detection on the warped sub-images to detect the ribs.

6. The method of claim 1, wherein suppressing the detected bones comprises:
  selecting one of the detected bones to suppress from the radiographic image;
  identifying a rectangular sub-image depicting the selected bone;
  clipping, from the rectangular sub-image, edges of selected bone positioned outside a lung region;
  processing the rectangular sub-image to reduce a curvature of the selected bone;

estimating a bone profile from the processed rectangular sub-image; and suppressing the bone profile from the radiographic image.

7. A method for performing bone suppression, the method comprising:

receiving a radiographic image;

detecting bones in the radiographic image, the detected bones comprising one or a combination of a clavicle bone, a posterior rib bone, and an anterior rib bone; and suppressing the detected bones in the radiographic image to generate a bone suppressed image, wherein suppressing the detected bones comprises:

selecting one of the detected bones to suppress from the radiographic image;

identifying a rectangular sub-image depicting the selected bone;

clipping, from the rectangular sub-image, edges of selected bone positioned outside a lung region;

processing the rectangular sub-image to reduce a curvature of the selected bone;

estimating a bone profile from the processed rectangular sub-image; and suppressing the bone profile from the radiographic image, and wherein estimating the bone profile from the processed rectangular sub-image comprises:

removing a background signal from the processed rectangular sub-image, thereby generating a background-removed image;

identifying upper and lower edge profiles of the selected bone depicted by the background-removed;

estimating the bone profile in accordance with the upper and lower edge profiles; and estimating a bone edge signal for the selected bone based on the processed rectangular sub-image or the background-removed signal, wherein estimation of the bone edge signal is performed separately from estimation of the bone profile, wherein estimating the bone edge signal for the selected bone from the processed rectangular sub-image comprises:

obtaining a directional subsampled sub-image of the selected bone by subsampling the processed rectangular sub-image at a higher frequency in a direction that is parallel to the selected bone than in a direction that is perpendicular to the selected bone; and estimating the bone edge signal from the directional subsampled sub-image, wherein estimating the bone edge signal from the directional subsampled sub-image comprises:

morphologically processing the directional subsampled sub-image to obtain a processed directional subsampled sub-image;

smoothing the processed directional subsampled sub-image to obtain a smoothed directional subsampled sub-image; and estimating the bone edge signal from the smoothed directional subsampled sub-image, and wherein smoothing the processed directional subsampled sub-image comprises:

smoothing regions the processed directional subsampled sub-image using a smaller sigma value for regions within a threshold distance of a bone-edge than regions greater than the threshold distance from the bone-edge.

8. A method for performing bone suppression, the method comprising:

receiving, by a processor, a radiographic image;

performing, by the processor, lung segmentation on the radiographic image to generate a segmented lung image;

detecting, by the processor, clavicle bones in the segmented lung image;

detecting, by the processor, rib bones in the segmented lung image; and suppressing, by the processor, the detected bones from the radiographic image to generate a bone suppressed image, wherein detecting clavicle bones in the segmented lung image comprises warping the segmented lung image to generate a warped image, wherein the clavicle bones are depicted with less curvature in the warped image than in the segmented lung image; and performing edge detection in the warped image to detect the clavicle bones.

9. The method of claim 8, wherein performing lung segmentation on the radiographic image to generate a segmented lung image comprises:

identifying, by the processor, region of interest (ROI) boundaries within the radiographic image;

identifying, by the processor, lung boundaries in accordance with the ROI boundaries; and merging, by the processor, the lung boundaries to generate a segmented lung image.

10. The method of claim 8, wherein detecting the rib bones in the segmented lung image comprises:

generating angle maps for the rib bones in the radiographic image, wherein a different one of the angle maps is generated for each of the rib bones;

warping portions of the radiographic image depicting the rib bones in accordance with a corresponding one of the angle maps to generate a plurality of warped sub-images, wherein the rib bones are depicted with less curvature in the plurality of warped sub-images than in the radiographic image; and performing edge detection on the warped sub-images to detect the rib bones.

11. The method of claim 8, wherein suppressing the detected bones from the radiographic image to generate the bone suppressed image comprises:

iteratively suppressing each of the detected bones on a bone-by-bone basis.

* * * * *